(12) United States Patent
Brahmbhatt et al.

(10) Patent No.: US 9,987,377 B2
(45) Date of Patent: *Jun. 5, 2018

(54) TARGETED GENE DELIVERY TO NON-PHAGOCYTIC MAMMALIAN CELLS VIA BACTERIALLY DERIVED INTACT MINICELLS

(71) Applicant: EnGeneIC Molecular Delivery Pty Ltd., Sydney (AU)

(72) Inventors: Himanshu Brahmbhatt, Sydney (AU); Jennifer MacDiarmid, Sydney (AU)

(73) Assignee: EnGeneIC Molecular Delivery Pty Ltd, Sydney (AU)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/820,464

(22) Filed: Aug. 6, 2015

(65) Prior Publication Data

US 2015/0343092 A1 Dec. 3, 2015

Related U.S. Application Data

(62) Division of application No. 10/581,990, filed as application No. PCT/IB2004/004406 on Dec. 8, 2004, now Pat. No. 9,169,495.

(60) Provisional application No. 60/527,764, filed on Dec. 9, 2003.

(51) Int. Cl.
| | |
|---|---|
| *A61K 48/00* | (2006.01) |
| *A61K 39/395* | (2006.01) |
| *C12N 15/88* | (2006.01) |
| *A61K 47/69* | (2017.01) |
| *A61K 39/00* | (2006.01) |

(52) U.S. Cl.
CPC ...... *A61K 48/0025* (2013.01); *A61K 39/3955* (2013.01); *A61K 47/6901* (2017.08); *A61K 48/0008* (2013.01); *A61K 48/0041* (2013.01); *C12N 15/88* (2013.01); *A61K 48/00* (2013.01); *A61K 2039/523* (2013.01); *C07K 2318/10* (2013.01); *C07K 2319/035* (2013.01); *C12N 2810/851* (2013.01); *C12N 2810/859* (2013.01)

(58) Field of Classification Search
CPC ................ A61K 48/00; A61K 48/0041; A61K 47/48776; C12N 15/88
See application file for complete search history.

(56) References Cited

U.S. PATENT DOCUMENTS

| | | | | |
|---|---|---|---|---|
| 5,221,479 A | * | 6/1993 | Etoh ................... | B01D 61/147 210/636 |
| 6,635,448 B2 | | 10/2003 | Bucciarelli et al. | |
| 7,011,946 B2 | | 3/2006 | RayChaudhuri et al. | |
| 7,125,679 B2 | | 10/2006 | Ashkar | |
| 7,183,105 B2 | * | 2/2007 | Sabbadini ............. | C12N 15/00 424/93.1 |
| 9,017,986 B2 | * | 4/2015 | Sabbadini ............. | C12N 15/00 435/252.1 |
| 2003/0004123 A1 | | 1/2003 | Boucher et al. | |
| 2003/0105310 A1 | | 6/2003 | Ashkar | |
| 2003/0190749 A1 | | 10/2003 | Surber et al. | |
| 2003/0194714 A1 | | 10/2003 | Sabbadini et al. | |
| 2003/0203481 A1 | | 10/2003 | Surber et al. | |
| 2004/0265994 A1 | | 12/2004 | Brahmbhatt et al. | |
| 2007/0241067 A1 | | 10/2007 | Brahmbhatt et al. | |
| 2007/0298056 A1 | | 12/2007 | Brahmbhatt et al. | |
| 2008/0038296 A1 | | 2/2008 | Brahmbhatt et al. | |
| 2008/0051469 A1 | | 2/2008 | Brahmbhatt et al. | |
| 2008/0299084 A1 | | 12/2008 | Brahmbhatt et al. | |

FOREIGN PATENT DOCUMENTS

| | | |
|---|---|---|
| JP | 10-505327 | 5/1998 |
| JP | 2002-531134 | 9/2002 |
| JP | 2003-055398 | 2/2003 |
| WO | WO 00/063364 A2 | 10/2000 |
| WO | WO 2003/002609 | 1/2003 |
| WO | WO 2003/033519 A2 | 4/2003 |
| WO | WO 2003/072014 A2 | 9/2003 |
| WO | WO 2005/056749 A2 | 6/2005 |
| WO | WO 2006/066048 A2 | 6/2006 |

OTHER PUBLICATIONS

Nettelbeck et al Mol Ther. 2001; 3(6):882-91.*
Coldwell et al The Journal of Immunology, 1984, 133, 2 950-957).*
Sundaram et al. 1999, PDA J. of Pharmaceutical Science and Technology, vol. 53(4), pp. 186-201.*
Forbes M. 1987, Australian J. Biotechnology, vol. 1(1), pp. 30-33.*
Beveridge et al (J of Bacteriology, 1999, 4725-4733.*
Notice of Allowance issued in related U.S. Appl. No. 10/581,990, dated Jun. 26, 2015.
Aline Jaffe et al., "Minicell-Forming Mutants of *Escherichia coli*: Production of Minicells and Anucleate Rods", Journal of Bacteriology, vol. 170, No. 7, Jul. 1988, pp. 3094-3101.
Anne Cornish Frazer et al., "Production, Properties and Utility of Bacterial Minicells", Current Topics in Microbiology and Immunology, Springer, Berlin, DE, vol. 69, Jan. 1, 1975, pp. 1-84.
Catherine Grillot-Courvalin et al., "Wild-type intracellular bacteria delivery DNA into mammalian cells," Cellular Microbiology, vol. 4, No. 3, (2002), pp. 177-186.

(Continued)

*Primary Examiner* — Anoop K Singh
(74) *Attorney, Agent, or Firm* — Foley & Lardner LLP

(57) ABSTRACT

A method of targeting bacterially-derived, intact minicells to specific, non-phagocytic mammalian cells employs bispecific ligands to deliver nucleic acids efficiently to the mammalian cells. Bispecific ligands, comprising (i) a first arm that carries specificity for a bacterially-derived minicell surface structure and (ii) a second arm that carries specificity for a non-phagocytic mammalian cell surface receptor are useful for targeting minicells to specific, non-phagocytic mammalian cells and causing endocytosis of minicells by non-phagocytic cells.

14 Claims, 7 Drawing Sheets

(56) References Cited

OTHER PUBLICATIONS

Christoph Mamot et al., "Epidermal Growth Factor Receptor (EGFR)-targeted Immunoliposomes Mediate Specific and Efficient Drug Delivery to EGFR- and EGFRvIII-overexpressing Tumor Cells", Cancer Research, Jun. 2003, vol. 63, 3154-3161.
Dawn E. Colwell et al., "Monoclonal Antibodies to *Salmonella* Lipopolysaccharide: Anti-O-Polysaccharide Antibodies Protect C3H Mice Against Challenge with Virulent *Salmonella typhimurium*," The Journal of Immunology, vol. 133, No. 2, Aug. 1984, pp. 950-957.
Dirk M. Nettelbeck et al.,"Targeting of Adenovirus to Endothelial Cells by a Bispecific Single-Chain Diabody Directed against the Adenovirus Fiber Knob Domain and human Endoglin (CD105)", Molecular Therapy vol. 3, No. 6, Jun. 2001, pp. 882-891.
Emmanouil D. Karagiannis et al., "Minicells overcome tumor drug-resistance", Nature Biotechnology, vol. 27, No. 7, Jul. 2009, pp. 620-621.
Esteban Veiga et al., "The role of clathrin-dependent endocytosis in bacterial internalization", Trends in Cell Biology, vol. 16, No. 10, pp. 499-504.
European Search Report EP 10 18 1873 dated Jan. 24, 2011.
Examination Report India Application No. 1866/KOLNP/2006 dated Oct. 26, 2009.
Gary J. Doherty et al., "Mechanisms and Endocytosis", Annu. Rev. Biochem. Mar. 14, 2009,78:31.1-31.46.
George G. Khachatourians, "Minicells as Specialized Vaccines and Vaccine Carriers", Recombinant DNA Vaccines: Rationale and Strategy, Dekker, New York, NY, US, Jan. 1, 1992, pp. 323-333.
H. Brahmbhatt et al., U.S. PTO Notice of Allowance, U.S. Appl. No. 10/602,021 dated Jun. 22, 2009, 5 pgs.
H. Brahmbhatt et al., U.S. PTO Office Action, U.S. Appl. No. 10/588,028 dated Mar. 18, 2009, 22 pgs.
H. Brahmbhatt et al., U.S. PTO Office Action, U.S. Appl. No. 10/602,021 dated May 4, 2006, 10 pgs.
H. Brahmbhatt et al., U.S. PTO Office Action, U.S. Appl. No. 10/602,021 dated May 15, 2007, 10 pgs.
H. Brahmbhatt et al., U.S. PTO Office Action, U.S. Appl. No. 10/602,021 dated Jul. 25, 2008, 10 pgs.
H. Brahmbhatt et al., U.S. PTO Office Action, U.S. Appl. No. 11/211,098 dated Feb. 24, 2009, 24 pgs.
H. Brahmbhatt et al., U.S. PTO Office Action, U.S. Appl. No. 11/211,098 dated Apr. 24, 2008, 38 pgs.
H. Brahmbhatt et al., U.S. PTO Office Action, U.S. Appl. No. 11/211,098 dated Aug. 7, 2009, 23 pgs.
H. Brahmbhatt et al., U.S. PTO Office Action, U.S. Appl. No. 11/691,698 dated Dec. 24, 2008, 13 pgs.
H. Brahmbhatt et al., U.S. PTO Office Action, U.S. Appl. No. 11/765,635 dated Oct. 6, 2009, 40 pgs.
H. Brahmbhatt et al., U.S. PTO Office Action, U.S. Appl. No. 12/053,197 dated Aug. 25, 2009, 25 pgs.
Hao Wu et al., "Small Interfereing RNA-induced Supression of MDR1 (P-Glycoprotein) Restores Sensitivity to Multidrug-resistant Cancer Cells", Cancer Research, 63, 1515-1519, Apr. 1, 2003.
Ian Tomlinson et al., "[28] Methods for Generating Multivalent and Bispecific Antibody Fragments", Multivalent and Bispecific Antibody Fragments, Methods in Enzymology, vol. 326, pp. 461-479, 2000.
Igor Dmitriev et al., "Ectodomain of Coxsackievirus and Adenovirus Receptor Genetically Fused to Epidermal Growth Factor Mediates Adenovirus Targeting to Epidermal Growth Factor Receptor-Positive Cells", Journal of Virology, Aug. 2000, vol. 74, No. 15, pp. 6875-6884.
Inder M. Verma et al., "Gene Therapy: Twenty-First Century Medicine", Annu. Rev. Biochem. 2005, 74:711-738.
J. H. Hong et al., "Antisense Bc12 oligonucleotide in cisplatin-resistant bladder cancer cell lines," BJU International, vol. 90, (2002), pp. 113-117.
Javier Pizarro-Cerdá et al., "Bacterial Adhesion and Entry into Host Cells", Cell 124, Feb. 24, 2006, pp. 715-727.

Jean-Remi Bertrand et al., "Comparison of antisense oligonucleotides and siRNAS in cell culture and in vivo," Biochemical and Biophysical Research Communications, vol. 296, (2002), pp. 1000-1004.
Jennifer A. MacDiarmid et al., "Bacterially Derived 400 nm Particles for Encapsulation and Cancer Cell Targeting of Chemotherapeutics", Cancer Cell 11, May 2007, pp. 431-445.
L. R. Kelland, "Of mice and men": values and liabilities of the athymic nude mouse model in anticancer drug development, European Journal of Cancer, vol. 40, (2004), pp. 827-836.
Leoni A. Kunz-Schughart et al., "The Use of 3-D Cultures for High-Throughput Screening: The Multicellular Spheriod Model," Journal of Biomolecular Screening, vol. 9, (2004), pp. 273-285.
Letter from Knobbe Martens Olson & Bear LLP dated Feb. 26, 2010.
Manfred Ogris et al., "Targeting tumors with non-viral gene delivery system", Drug Discovery Today, vol. 7, No. 8, Apr. 14, 2002, pp. 479-485.
Manisha P. Desai et al., "The Mechanism of Uptake of Biodegradable Microparticles in Caco-2 Cells is Size Dependent", Pharmaceutical Research, vol. 14, No. 11, 1997, pp. 1568-1573.
Masahisa Watarai et al., "Interaction of Ipa Proteins of *Shigella flexneri* with $\alpha_5\beta_1$ Integrin Promotes Entry of the Bacteria into Mammalian Cells", J. Exp. Med. vol. 183, Mar. 1996, pp. 991-999.
Michael J. McCluskie et al., "Route and Method of Delivery of DNA Vaccine Influence Immune Responses in Mice and Non-Human Primates," Molecular Medicine, vol. 5, (1999), pp. 287-300.
Michele Carbone et al., "Multistep and multifactorial carcinogenesis: when does a contributing factor become a carcinogen?," Seminars in Cancer Biology, vol. 14, (2004) pp. 399-405.
Michele De Palma et al., "In Vivo Targeting of Tumor Endothelial Cells by Systemic Delivery of Lentiviral Vectors," Human Gene Therapy, vol. 14, Aug. 10, 2003, pp. 1193-1206.
Mickey Pentecost et al., "*Listeria monocytogenese* Internalin B Activates Junction Endocytosis to Accelerate Intestinal Invasion", PLoS Pathogens, vol. 6, Issue 5, May 2010, document e1000900, 15 pgs.
Pascal Peschard, "Escape from Cbl-mediated downregulation: A recurrent theme for oncogenic deregulation of receptor tyrosine kinases", Cancer Cell, Jun. 2003, vol. 3, pp. 519-523.
Richard J. Cristiano et al., "Strategies to accomplish gene delivery via the receptor-mediated endocytosis pathway", Cancer Gene Therapy, vol. 3, No. 1, 1996, pp. 49-57.
Robert M. Smith et al., "Hepatocyte-directed Gene Delivery by Receptor-mediated Endocytosis", Seminars in Liver Disease, vol. 19, No. 1, 1999, pp. 83-92.
Robert S. Kerbel, "What is the optimal rodent model for anti-tumor drug testing?," Cancer and Metastasis Reviews, vol. 17, (1999), pp. 301-304.
Sean D. Conner et al., "Regulated portals of entry into the cell", Nature, vol. 422, Mar. 6, 2003, pp. 37-44.
Sharon I. Michael et al., "Strategies to achieve targeted gene delivery via the receptor-mediated endocytosis pathway", Gene Therapy (1994) 1, pp. 223-232.
Stephen L. Eck et al., "Gene-Based Therapy," Chapter 5, Goodman & Gilman's The Pharmacological Basis of Therapeutics, (1996), pp. 77-102.
Thomas J. Wickham et al., "Targeted Adenovirus Gene Transfer to Endothelial and Smooth Muscle Cells by Using Bispecific Antibodies", Journal of Virology, the American Society for Microbiology, US, vol. 70, No. 10, Oct. 1996, pp. 6831-6838.
Thomas L. Hale et al., "Characterization of Virulence Plasmids and Plasmid-Associated Outer Membrane Proteins in *Shigella flexneri, Shigella sonnei*, and *Escherichia coli*", Infection and Immunity, Apr. 1983, vol. 40, No. 1, pp. 340-350.
Tibor Pal et al., "Plasmid-Associated Adherence of *Shigella flexneri* in a HeLa Cell Model", Infection and Immunity, Aug. 1989, vol. 57, No. 8, pp. 2580-2582.
William F. Scherer et al., "Studies of the Propagation In Vitro of Poliomyelitis Viruses", Journal of Experimental Medicine, vol. 97, No. 5, pp. 695-710 (1953).
William F. Scherer M.D. et al., "The Viral Range In Vitro of a Malignant Human Epithelial Cell (Strain Hela, Gey)—III. Studies

(56) References Cited

OTHER PUBLICATIONS with Pseudolymphocytic Choriomeningitus Virus General Discussion", American Journal of Pathology, Jan-Feb 31(1): 31-39 (1954).
Yi Lu et al., "Delivery of adenoviral vectors to the prostate for gene therapy," Cancer Gene Therapy, vol. 6, No. 1, (1999), pp. 64-72.
Jagath L. Kadurugamauwa et al., "Virulence Factors Are Released from *Pseudomonas aeruginosa* in Association with Membrane Vesicles during Normal Growth and Exposure to Gentamicin: a Novel Mechanism of Enzyme Secretion", Journal of Bacteriology, Jul. 1995, vol. 177, No. 14, pp. 3998-4008.
Final Office Action U.S. Appl. No. 12/019,090 dated Sep. 15, 2010.
Advisory Action U.S. Appl. No. 12/019,090 dated Jun. 8, 2011.
Grillot-Courvalin et al., "Bacteria as Gene Delivery Vectors for Mammalian Cells," Current Opinion in Biotechnology 1999, 10: 477-481.
Khatchatourians et al., "A New Method for the Preparation of Minicells for Physiological Studies," Preparative Biochemistry, 3(3) 1973, 291-298.
Christen et al., "Rapid Isolation of *Eschericia coli* minicells by glass-fiber filtration: study of plasmid-coded polypeptides," Gene, 1983, 23, 195-198.
Beveridge et al., "Structures of Gram-Negative Cell Walls and Their Derived Membrane Vesicles," Journal of Bacteriology, 1999, 4725-2733.
Forbes M., "Crossflow Microfiltration," (Australian J. Biotechnology, 1987, 1(1), 30-33.

\* cited by examiner

Figure 4
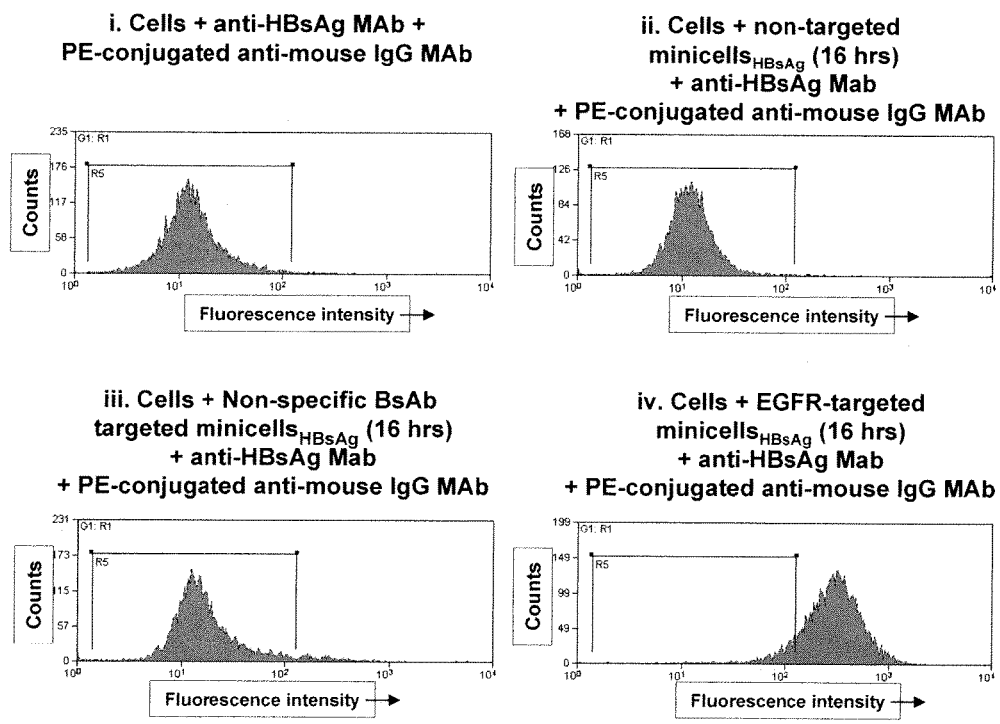
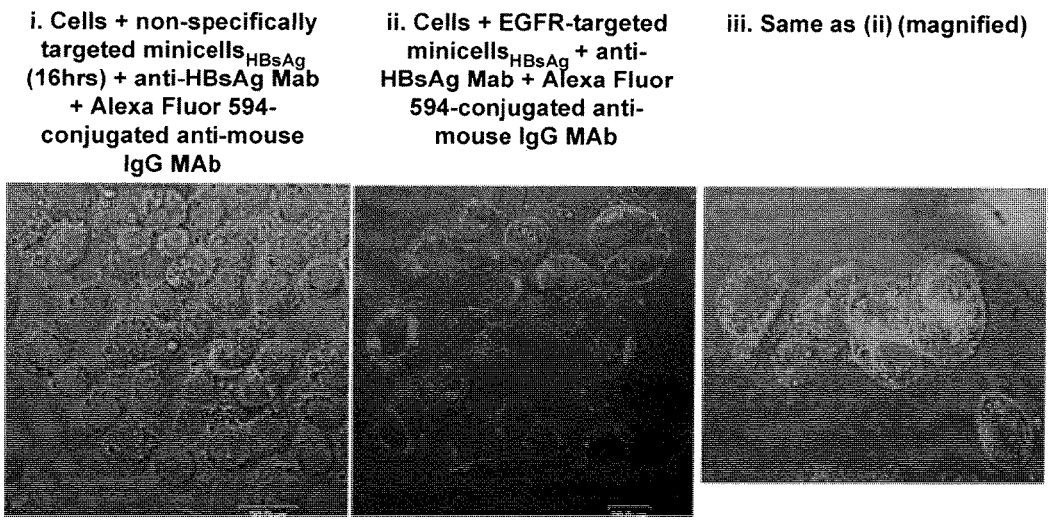

TARGETED GENE DELIVERY TO NON-PHAGOCYTIC MAMMALIAN CELLS VIA BACTERIALLY DERIVED INTACT MINICELLS

CROSS-REFERENCE TO RELATED APPLICATIONS

This application is a divisional of U.S. patent application Ser. No. 10/581,990, filed Feb. 26, 2007, which is a national stage application of PCT/IB2004/004406, filed Dec. 8, 2004, which claims the benefit of priority from U.S. Provisional Patent Application No. 60/527,764, filed Dec. 9, 2003, the disclosures of which are incorporated herein by reference in their entirety.

BACKGROUND OF THE INVENTION

The present invention relates to methods and compositions for targeting bacterial minicell vectors to non-phagocytic host cells, particularly but not exclusively in the context of gene therapy. The invention employs bispecific molecules that specifically bind to both a minicell surface structure and a host cell surface structure, such as a receptor. By mediating an interaction between the minicell vectors and non-phagocytic host cells, the bispecific ligands enable targeted delivery of oligonucleotides and polynucleotides to the host cells.

The objective of gene therapy is to insert one or more foreign genes into the cells of an organism to shut down a gene, to replace a defective gene, or to express a gene product that provides a prophylactic or therapeutic effect. Recent advances in gene therapy have highlighted a variety of methods for introducing foreign genes into the genome of recipient mammals. See Romano et al. 1998, 1999; Balicki and Beutler, 2002; Wadhwa et al., 2002; and Thomas et al., 2003. These advances relate to using viral vectors, both human and non-human, and non-viral vectors, such as DNA-liposome complexes.

While each vector system has its advantages, each also has significant drawbacks that have limited any clinical application. In particular, viral vectors pose serious safety concerns, including recombination with wild-type viruses, insertional and oncogenic potential, intrinsic toxicity of animal virus vectors to mammalian cells, virus-induced immunosuppression, reversion to virulence of attenuated viruses, and adverse reactions such as an inflammatory response caused by existing immunity. Viral vectors also present practical problems, such as difficulties in recombinant virus manufacture and distribution, low stability, and limited capacity of the vectors to carry large amounts of exogenous DNA. Non-viral vectors have the drawbacks of generally being less efficient at gene delivery.

Addressing these drawbacks, PCT/IB02/04632 described recombinant, intact minicells that contain therapeutic nucleic acid molecules. Such minicells are effective vectors for delivering oligonucleotides and polynucleotides to host cells in vitro and in vivo. PCT/IB02/04632 demonstrated, for example, that recombinant minicells carrying mammalian gene expression plasmids could be delivered to phagocytic cells, such as macrophages, and to non-phagocytic cells, illustrated by human breast cancer cells. The application also showed that intraperitoneal administration of the recombinant minicells resulted in recombinant plasmid delivery to phagocytic cells of the immune system, and that a serum antibody response to the encoded protein could be elicited.

While the efficiency of gene delivery to phagocytic cells via minicells is high (40-60%), the efficiency of gene delivery to non-phagocytic cells heretofore has been comparatively low (3% to 5%). This would be expected severely to limit clinical applications, because many potential indications for gene therapy involve endothelial and other non-phagocytic cells. Most cancers, for instance, are not of phagocytic cells, and one would not expect that vectors lacking cell- or organ-specificity could effectively be employed for treating such cancers.

A similar lack of specificity also has hindered the application of non-minicell vectors, and various approaches are under development to address this problem. See Wickham, 2003. One approach makes use of the receptor-mediated endocytosis (RME) system, present in many cell types, and entails development of a diverse set of targeting ligands. In this approach, cell-specificity is imparted to the vector by linking it to a ligand that targets a specific cell surface receptor or marker. Following the specific binding, target cell RME system is activated and the vector/receptor complex is internalized and digested, with some of the DNA payload being transported to the nucleus for gene expression. Some cell receptors may be able to facilitate vector uptake into the cytoplasm directly across the plasma membrane (Fernandez and Bailey, 1998; Phelan et al., 1998; Rojas et al., 1998), but the most common route for receptor-mediated uptake of macromolecular moieties is the endocytic-trafficking pathway (Conner and Schmid, 2003).

Several challenges exist regarding targeted gene delivery to non-phagocytic mammalian cells: (i) breaching the mammalian cell plasma membrane; (ii) exploiting a mechanism of delivery vector internalization; (iii) selecting and understanding the nature of targeting ligands used to target specific mammalian cell surface receptors; (iv) achieving intracellular breakdown of the delivery vector without complete degradation of payload DNA; and (v) obtaining release and transport of payload DNA to the mammalian cell cytoplasm or nucleus. These challenges vary somewhat with each gene delivery vector. Despite intensive research in the field, detailed knowledge of the biological processes involved still is rudimentary.

Ligand-based targeting of bacterial cells or any particles of bacterial origin to non-phagocytic cells has not been reported, probably because (a) only live bacterial intracellular pathogens can gain entry into non-phagocytic cells, though this is achieved by an active invasion process (i.e., entry into non-phagocytic cells is thought to be an active invasion process that requires a multicomponent energy driven process performed by live bacterial pathogens) and (b) active cellular invasion would override a passive process such as ligand-based receptor mediated endocytosis. Thus, killed bacterial cells would not engage in active cell invasion, and live bacterial cells would not be directed, contrary to their natural tropism, toward desired non-phagocytic cells. Even if ligand-based targeting was employed to enable endocytosis of killed bacterial cells or non-living particles of bacterial origin, the method would not be expected to be effective for gene delivery. Rather, it would be expected that endosomes would degrade the non-living cells or particles, making them ineffective as gene delivery vectors. In that regard, it currently is thought that only live facultative intracellular pathogenic bacteria can express proteins that allow escape from the endosomal membrane.

To date, no proven methodology exists for effectively targeting bacterial minicell vectors to non-phagocytic mammalian host cells, thereby to deliver a gene payload. Although a variety of vector targeting technologies are known, simply adopting any one of them does not predictably result in a successful, minicell-targeted gene delivery. This is due to the range of biological factors, unique for each gene delivery vector, that can influence targeted gene delivery.

Therefore, a need exists for a method of specifically targeting bacterial minicell vectors to non-phagocytic mammalian cells.

SUMMARY OF THE INVENTION

To address these and other needs, the present invention provides, in accordance with one aspect, a targeted gene delivery method that comprises bringing bispecific ligands into contact with (i) bacterially derived minicells that contain a therapeutic nucleic acid sequence and (ii) non-phagocytic mammalian cells. The ligands have specificity for both a surface component on the minicells and a surface component on the non-phagocytic mammalian cells. As a result, the minicells are engulfed by the mammalian cells, which then produce an expression product of the therapeutic nucleic acid sequence. Contact between the minicells and the mammalian cells may be in vitro or in vivo.

The invention also provides bispecific ligands useful for targeting minicell vectors to non-phagocytic mammalian host cells. The bispecific ligand may be polypeptide or carbohydrate, and may comprise an antibody or antibody fragment. In preferred embodiments, the bispecific ligand has a first arm that carries specificity for a bacterial minicell surface structure and a second arm that carries specificity for a non-phagocytic mammalian cell surface structure. A desirable minicell surface structure for ligand binding is an O-polysaccharide component of a lipopolysaccharide. Desirable mammalian cell surface structures for ligand binding are receptors, preferably those capable of activating receptor-mediated endocytosis.

In another aspect, the invention provides a composition comprising (i) bacterially derived minicells that contain a therapeutic nucleic acid and (ii) bispecific ligands that are capable of binding to a surface component of the minicells and a surface component of a non-phagocytic mammalian cell.

In still another aspect, the invention provides for the use of bacterially derived minicells that contain a therapeutic nucleic acid and a bispecific ligand in the preparation of a medicament for use in a method of treating a disease or modifying a trait by administration of the medicament to a cell, tissue, or organ. Such medicaments are useful to treat various conditions and diseases by increasing expression or function of a desired protein, or by inhibiting expression or function of a target protein. The disease to be treated in this context may be a cancer, for example, or an acquired disease, such as AIDS, pneumonia, emphysema, or a condition engendered by an inborn error of metabolism, such as cystic fibrosis. Alternatively, the treatment may affect a trait, such as fertility, or an immune response associated with an allergen or an infectious agent.

The result showed intense red fluorescence in the cytoplasm of most cells (light grey in the image). Scale bars are shown for each image.

FIG. 4 shows the efficiency of gene delivery to human breast cancer (MDA-MB-468) cells using EGFR-targeted minicells carrying a plasmid encoding the viral Hepatitis B Surface antigen. (A) Flow Cytometry results showing fluorescence intensity of cells treated with (i) anti-HBsAg MAb followed by Phycoerythrin (PE)-conjugated secondary antibody (anti-mouse IgG), (ii) non-targeted minicells followed by anti-HBsAg MAb and PE-conjugated anti-mouse IgG MAb, (iii) non-specifically targeted minicells followed by anti-HBsAg MAb and PE-conjugated anti-mouse IgG MAb, and (iv) EGFR-targeted minicells followed by anti-HBsAg MAb and PE-conjugated anti-mouse IgG MAb. (B) Confocal microscopy results showing efficient gene delivery and recombinant HBsAg expression in MDA-MB-468 cells following transfection with EGFR-targeted minicells$_{HBsAg}$ (ii and iii). The intense intracellular red fluorescence (shows as light grey in black and white image) is the recombinant HBsAg protein revealed with anti-HBsAg MAb followed by Alexa Fluor 594-conjugated anti-mouse IgG MAb. Control cells (i) that were transfected with non-specifically targeted minicells$_{HBsAg}$ showed only a couple of background red fluorescence dots.

Figure 5:
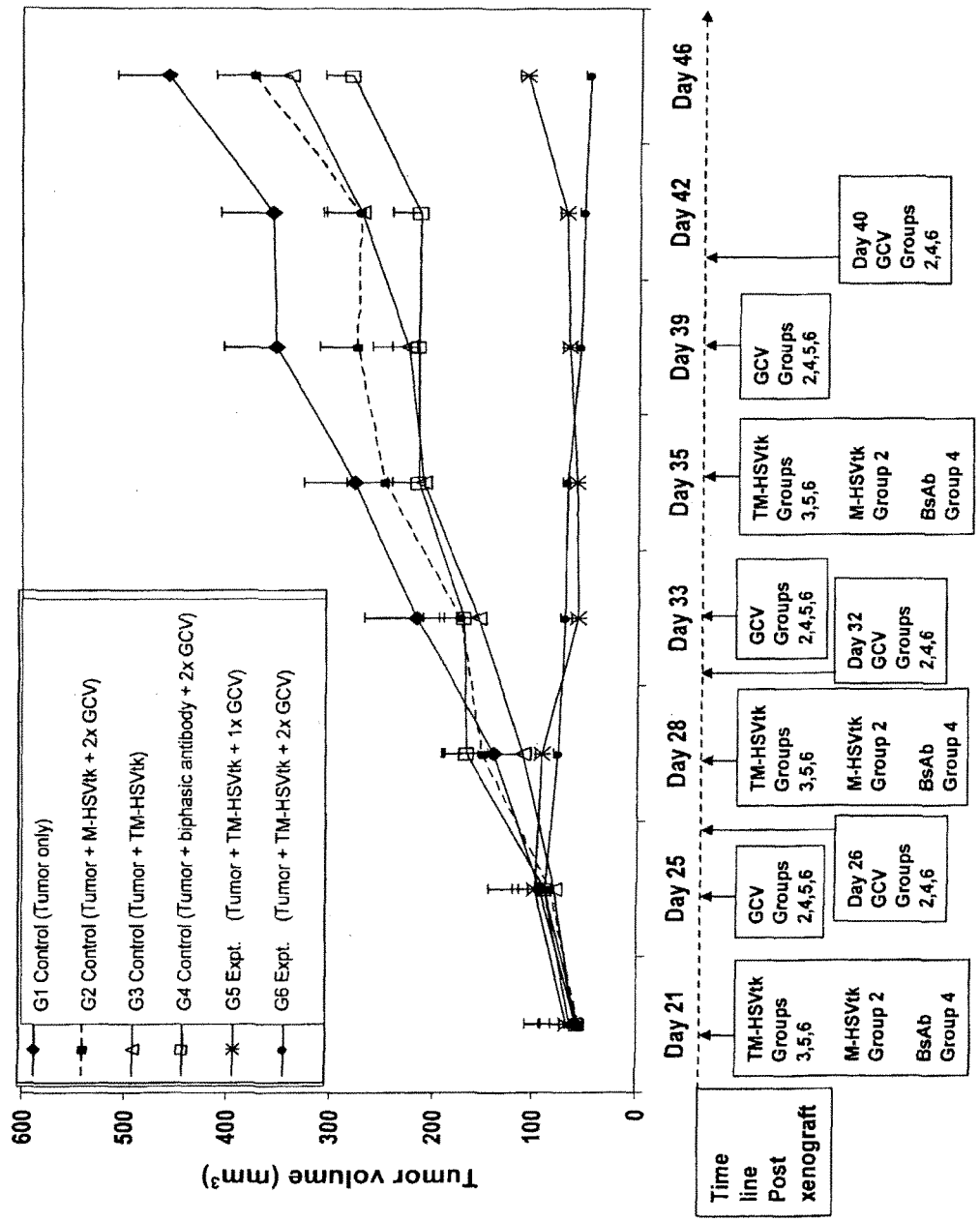

FIG. 5 shows treatment of human breast cancer xenografts in nude mice via targeted recombinant minicells. Breast cancer xenografts were established in nude mice (see example 5) and treated intratumorally with targeted recombinant minicells carrying plasmid pORF5-HSV1tk::Sh ble. (Group 1, control) tumors did not receive any treatment; (Group 2, control) tumors were treated with non-targeted recombinant minicells [M-HSVtk] followed by 2 doses of GCV; (Group 3, control) tumors were treated with targeted recombinant minicells [TM-HSVtk]; (Group 4, control) tumors were treated with the bispecific antibody (BsAb; anti-S. typhimurium LPS/anti-human EGF receptor specificities), followed by 2 doses of GCV; (Group 5, experimental) tumors were treated with targeted recombinant minicells [TM-HSVtk] followed by one dose of GCV; (Group 6, experimental) tumors were treated with targeted recombinant minicells [TM-HSVtk] followed by 2 doses of GCV. Below the x-axis are shown the days on which various treatments were given to specific groups.

Figure 6:
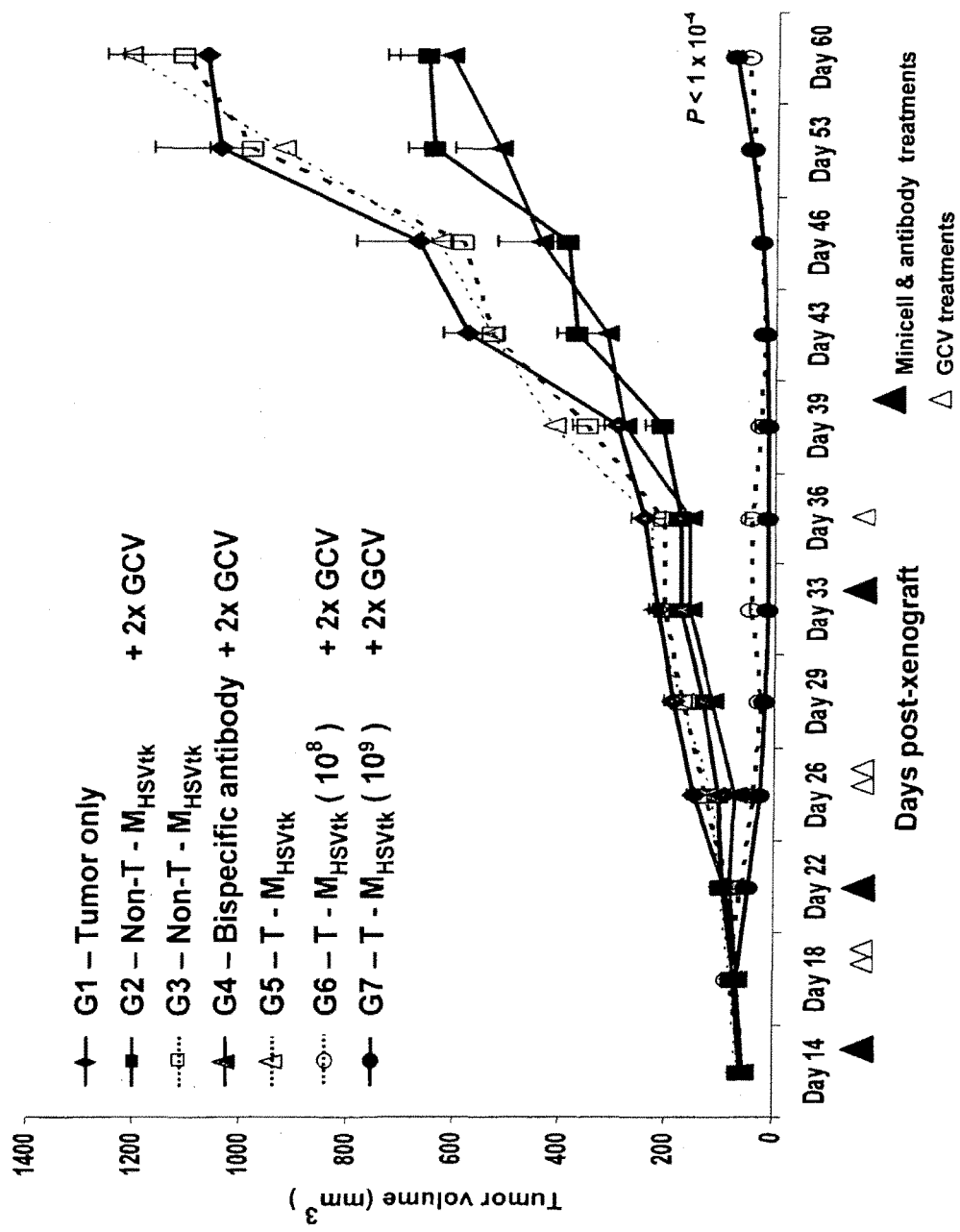

FIG. 6 shows treatment of human breast cancer xenografts in nude mice via recombinant minicells targeted to an over-expressed EGF receptor. Breast cancer xenografts were established in nude mice (see example 6) and treated intravenously with targeted recombinant minicells carrying plasmid pORF5-HSV1tk::Sh ble. Tumor xenografts were treated as follows: (Group 1, control) no treatment; (Group 2, control) non-targeted recombinant minicells [non-T-M$_{HSVtk}$] followed by 2 doses of GCV, (Group 3, control) non-targeted recombinant minicells [non-T-M$_{HSVtk}$], (Group 4, control) bispecific antibody (BsAb; anti-S. typhimurium LPS/anti-human EGF receptor specificities), followed by 2 doses of GCV, (Group 5, control) targeted recombinant minicells [T-M$_{HSVtk}$], (Group 6, experimental) $10^8$ targeted recombinant minicells [T-M$_{HSVtk}$] followed by 2 doses of GCV, and (Group 7, experimental) $10^9$ targeted recombinant minicells [T-M$_{HSVtk}$] followed by 2 doses of GCV. Below the x-axis are shown the days on which various treatments were given to specific groups. Closed triangles indicate minicell or antibody treatments and open triangles indicate GCV treatments.

Figure 7:
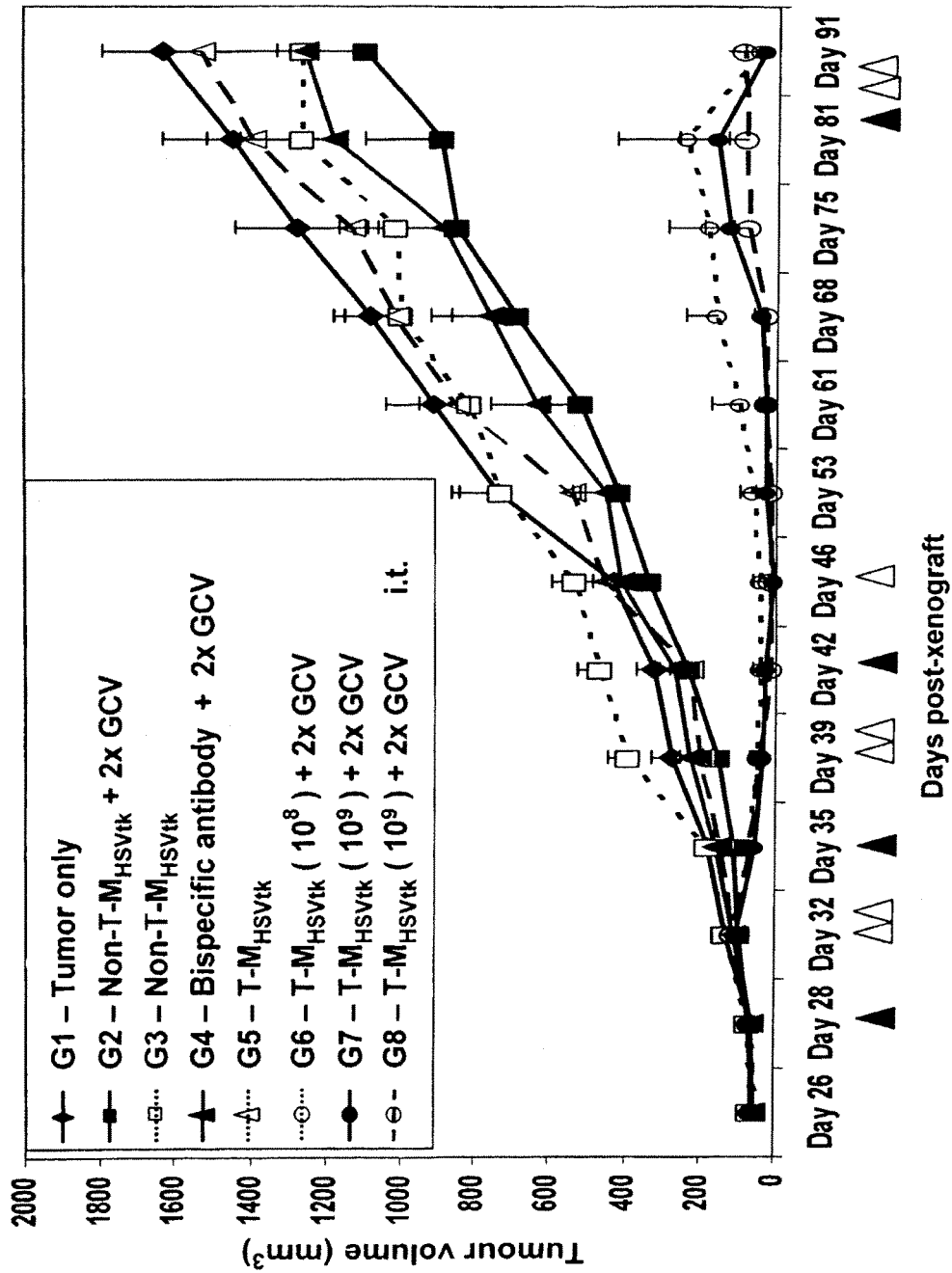

FIG. 7 shows treatment of human breast cancer xenografts in nude mice via recombinant minicells targeted to an under-expressed HER2/neu receptor. Breast cancer xenografts were established in nude mice (see example 5) and treated intravenously with targeted recombinant minicells carrying plasmid pORF5-HSV1tk::Sh ble. Group 8 mice were injected intratumorally with the recombinant minicells. Tumor xenografts were treated as follows: (Group 1, control) no treatment, (Group 2, control) non-targeted recombinant minicells [non-T-M$_{HSVtk}$] followed by 2 doses of GCV, (Group 3, control) non-targeted recombinant minicells [non-T-M$_{HSVtk}$], (Group 4, control) bispecific antibody (BsAb; anti-S. typhimurium LPS/anti-human HER2/neu receptor specificities), followed by 2 doses of GCV, (Group 5, control) targeted recombinant minicells [T-M$_{HSVtk}$], (Group 6, experimental) $10^8$ targeted recombinant minicells [T-M$_{HSVtk}$] followed by 2 doses of GCV, (Group 7, experimental) $10^9$ targeted recombinant minicells [T-M$_{HSVtk}$] followed by 2 doses of GCV, and (Group 8, experimental) intratumoral injection of $10^9$ targeted recombinant minicells [T-M$_{HSVtk}$] followed by 2 doses of GCV. Below the x-axis are shown the days on which various treatments were given to specific groups. Closed triangles indicate minicell or antibody treatments and open triangles indicate GCV treatments.

DETAILED DESCRIPTION OF THE PREFERRED EMBODIMENTS

The present inventors have discovered that bispecific ligands can be employed to target bacterial minicell vectors to non-phagocytic mammalian host cells. Such host cells normally are resistant to adhesion and endocytosis of minicells in vivo, yet can be made receptive to minicell delivery vector binding and internalization with the aid of a bispecific ligand.

Additionally, the inventors have discovered that the internalized minicells are degraded sufficiently to release recombinant plasmid DNA. This is surprising because non-phagocytic mammalian cells inherently do not carry aggressive intracellular compartments like phagolysosomes, which predominantly exist in cells of the immune system such as phagocytic macrophages.

As an additional surprise, the inventors also discovered that bacterial minicells can effect recombinant plasmid escape from the late-endosome of non-phagocytic cells. This is unexpected because minicells are non-living and devoid of the parent bacterial chromosome that encodes late-endosomal and phagosomal membrane-lysing proteins. Indeed, it had been commonly accepted that only live facultative intracellular bacterial pathogens designed to lyse the lysosomal membrane and release DNA intracellularly can deliver genes to non-professional phagocytes (reviewed recently by Grillot-Courvalin et al., 2002). For example, *Listeria monocytogenes* expresses a pore-forming cytolysin, Listeriolysin O (chromosomally encoded by the hly gene), that is thought to play a major role in lysing the endosomal and phagosomal membrane, thereby allowing recombinant DNA to enter an infected cell cytoplasm. Similarly, *Shigella flexneri* also is thought to escape the phagocytic vacuole by lysing the phagosomal membrane.

The inventors further have established that effective minicell-mediated recombinant gene delivery to the nucleus of non-phagocytic cells relates to the number of plasmid copies carried by a minicell. Thus, minicells carrying a high-copy number plasmids (over 60 plasmid copies per minicell) effect efficient gene delivery to non-phagocytic cells, whereas minicells carrying medium-copy (11 to 60 per minicell) or low-copy (1 to 10 per minicell) number plasmids are less effective.

Additionally, the inventors have established that efficiency of gene delivery relates to the number of minicells that are endocytosed within endosomes. Accordingly, non-phagocytic target cells that carry highly expressed receptors on the cell surface, such as EGF receptor on the surface of some human breast cancer cells, and to which the bispecific ligand was targeted, show more minicells engulfed within each endosome, often more than 10, resulting in highly efficient recombinant gene delivery to the cell nucleus. These results suggest that the chances for escape of recombinant DNA from late endosomes are increased when the recombinant DNA load within an endosome is high enough to compensate for losses through degradation within the endosome. The results also show that effective gene delivery may be achieved by exploiting mammalian cell surface receptors that are over-expressed on the cell surface, thereby enabling the endocytosis of multiple minicells within individual endosomes.

In accordance with the foregoing discoveries, the invention broadens the spectrum of diseases amenable to gene therapy using minicell vectors, by enhancing the minicell transfection efficiency in target cells or tissues that normally are refractory to minicell adhesion, endocytosis and gene delivery. The ability to target minicells also provides a safer and more flexible system for gene therapy.

In one aspect, therefore, the invention provides a targeted gene delivery method that comprises bringing bispecific ligands into contact with (a) bacterially derived minicells that contain a therapeutic nucleic acid sequence and (b) non-phagocytic mammalian cells. The bispecific ligands, having specificity for both minicell and mammalian cell components, cause the minicells to bind to the mammalian cells, such that the minicells are engulfed by the mammalian cells, which then produce an expression product of the therapeutic nucleic acid sequence.

The inventors found that this method is broadly applicable to a range of non-phagocytic mammalian cells that normally are refractory to specific adhesion and endocytosis of minicells. For example, bispecific antibody ligands with anti-O-polysaccharide specificity on one arm and anti-HER2 receptor, anti-EGF receptor or anti-androgen receptor specificity on the other arm efficiently bound minicells to the respective receptors on a range of non-phagocytic cells. These cells included lung, ovarian, brain, breast, prostate and skin cancer cells. Moreover, the efficient binding preceded rapid endocytosis of the minicells by each of the non-phagocytic cells.

The inventors' discovery is surprising because it previously was thought that only "professional" phagocytes, such as macrophages and neutrophils, can endocytose large macromolecular particles like bacterial cells, which are 600 nm and larger. Conversely, it was thought that non-phagocytic mammalian cells can endocytose only small, non-living macromolecular particles such as liposomes, which are 150-400 nm, and viruses, which are on the order of 65-80 nm in size. See Bondoc and Fitzpatrick, 1998. Bacterially derived intact minicells used in the inventors' studies were approximately 400 nm in diameter.

The inventors also found that recombinant DNA carried by minicells can be expressed by non-phagocytic mammalian host cells. The minicells, once endocytosed, subsequently become degraded in late endosomes. Some recombinant DNA carried by the minicells, however, escapes the endosomal membranes and is transported to the mammalian cell nucleus, permitting gene expression. This discovery is surprising because it previously was thought that only live facultative intracellular pathogens carry virulence proteins capable of endosomal membrane escape and gene delivery. See Grillot-Courvalin et al., 2002. Non-living bacteria or bacterially derived minicells were not expected to express these in vivo induced virulence proteins and, hence, were expected to be completely degraded within endosomes, with no possibility for endosomal escape by any recombinant DNA.

The invention therefore provides novel methods that extend the range of mammalian cells amenable to gene therapy via bacterially derived minicells. These methods may be performed both in vitro and in vivo.

Ligands useful in the invention include any agent that binds to a surface component on a target cell and to a surface component on a minicell. Preferably, the surface component on a target cell is a receptor, especially a receptor capable of mediating endocytosis. The ligands may comprise a polypeptide and/or carbohydrate component. Antibodies are preferred ligands. For example, a bispecific antibody that carries dual specificities for a surface component on bacterially derived intact minicells and for a surface component on target mammalian cells, can be used to efficiently target the minicells to the target mammalian cells in vitro and in vivo. Useful ligands also include receptors, enzymes, binding peptides, fusion/chimeric proteins and small molecules.

The selection of a particular ligand is made on two primary bases: (i) specific binding to one or more domains on the surface of intact minicells and (ii) specific binding to one or more domains on the surface of the target cells. Thus, ligands preferably have a first arm that carries specificity for a bacterially derived intact minicell surface structure and a second arm that carries specificity for a non-phagocytic mammalian cell surface structure. Each of the first and second arms may be multivalent. Preferably, each arm is monospecific, even if multivalent.

For binding to bacterially derived minicells, it is desirable for one arm of the ligand to be specific for the O-polysaccharide component of a lipopolysaccharide found on the parent bacterial cell. Other minicell surface structures that can be exploited for ligand binding include cell surface-exposed polypeptides and carbohydrates on outer membranes, pilli, fimbrae and flagella.

For binding to target cells, one arm of the ligand is specific for a surface component of a non-phagocytic mammalian cell. Such components include cell surface proteins, peptides and carbohydrates, whether characterized or uncharacterized. Cell surface receptors, especially those capable of activating receptor-mediated endocytosis, are desirable cell surface components for targeting.

By way of example, one may target tumor cells, metastatic cells, vasculature cells, such as endothelial cells and smooth muscle cells, lung cells, kidney cells, blood cells, bone marrow cells, brain cells, liver cells, and so forth, or precursors of any selected cell by selecting a ligand that specifically binds a cell surface receptor motif on the desired cells. Examples of cell surface receptors include carcinoembryonic antigen (CEA), which is overexpressed in most colon, rectum, breast, lung, pancreas and gastrointestinal tract carcinomas (Marshall, 2003); heregulin receptors (HER-2, neu or c-erbB-2), which is frequently overexpressed in breast, ovarian, colon, lung, prostate and cervical cancers (Hung et al., 2000); epidermal growth factor receptor (EGFR), which is highly expressed in a range of solid tumors including those of the breast, head and neck, non-small cell lung and prostate (Salomon et al., 1995); asialoglycoprotein receptor (Stockert, 1995); transferrin receptor (Singh, 1999); serpin enzyme complex receptor, which is expressed on hepatocytes (Ziady et al., 1997); fibroblast growth factor receptor (FGFR), which is overexpressed on pancreatic ductal adenocarcinoma cells (Kleeff et al., 2002); vascular endothelial growth factor receptor (VEGFR), for anti-angiogenesis gene therapy (Becker et al., 2002 and Hoshida et al., 2002); folate receptor, which is selectively overexpressed in 90% of nonmucinous ovarian carcinomas (Gosselin and Lee, 2002); cell surface glycocalyx (Batra et al., 1994); carbohydrate receptors (Thurnher et al., 1994); and polymeric immunoglobulin receptor, which is useful for gene delivery to respiratory epithelial cells and attractive for treatment of lung diseases such as Cystic Fibrosis (Kaetzel et al., 1997).

Preferred ligands comprise antibodies and/or antibody derivatives. As used herein, the term "antibody" encompasses an immunoglobulin molecule obtained by in vitro or in vivo generation of an immunogenic response. The term "antibody" includes polyclonal, monospecific and monoclonal antibodies, as well as antibody derivatives, such as single-chain antibody fragments (scFv). Antibodies and antibody derivatives useful in the present invention also may be obtained by recombinant DNA techniques.

Wild type antibodies have four polypeptide chains, two identical heavy chains and two identical light chains. Both types of polypeptide chains have constant regions, which do not vary or vary minimally among antibodies of the same class, and variable regions. Variable regions are unique to a particular antibody and comprise an antigen binding domain that recognizes a specific epitope. The regions of the antigen binding domain that are most directly involved in antibody binding are "complementarity-determining regions" (CDRs).

The term "antibody" also encompasses derivatives of antibodies, such as antibody fragments that retain the ability to specifically bind to antigens. Such antibody fragments include Fab fragments (a fragment that contains the antigen-binding domain and comprises a light chain and part of a heavy chain bridged by a disulfide bond), Fab' (an antibody fragment containing a single antigen-binding domain comprising a Fab and an additional portion of the heavy chain through the hinge region, F(ab')2 (two Fab' molecules joined by interchain disulfide bonds in the hinge regions of the heavy chains), a bispecific Fab (a Fab molecule having two antigen binding domains, each of which may be directed to a different epitope), and an scFv (the variable, antigen-binding determinative region of a single light and heavy chain of an antibody linked together by a chain of amino acids.)

When antibodies, including antibody fragments, constitute part or all of the ligands, they preferably are of human origin or are modified to be suitable for use in humans. So-called "humanized antibodies" are well known in the art. See, e.g., Osbourn et al., 2003. They have been modified by genetic manipulation and/or in vitro treatment to reduce their antigenicity in a human. Methods for humanizing antibodies are described, e.g., in U.S. Pat. No. 6,639,055, U.S. Pat. No. 5,585,089, and U.S. Pat. No. 5,530,101. In the simplest case, humanized antibodies are formed by grafting the antigen-binding loops, known as complementarity-determining regions (CDRs), from a mouse mAb into a human IgG. See Jones et al., 1986; Riechmann et al., 1988; and Verhoeyen et al., 1988. The generation of high-affinity humanized antibodies, however, generally requires the transfer of one or more additional residues from the so-called framework regions (FRs) of the mouse parent mAb.

Several variants of the humanization technology also have been developed. See Vaughan et al., 1998.

Human antibodies, rather than "humanized antibodies," also may be employed in the invention. They have high affinity for their respective antigens and are routinely obtained from very large, single-chain variable fragments (scFvs) or Fab phage display libraries. See Griffiths et al., 1994; Vaughan et al., 1996; Sheets et al., 1998; de Haard et al., 1999; and Knappik et al., 2000.

Useful ligands also include bispecific single chain antibodies, which typically are recombinant polypeptides consisting of a variable light chain portion covalently attached through a linker molecule to a corresponding variable heavy chain portion. See U.S. Pat. Nos. 5,455,030; 5,260,203 and 4,496,778. Bispecific antibodies also can be made by other methods. For example, chemical heteroconjugates can be created by chemically linking intact antibodies or antibody fragments of different specificities. See Karpovsky et al., 1984. such heteroconjugates are difficult to make in a reproducible manner, however, and are at least twice as large as normal monoclonal antibodies. Bispecific antibodies also can be created by disulfide exchange, which involves enzymatic cleavage and reassociation of the antibody fragments. See Glennie et al., 1987.

Because Fab and scFv fragments are monovalent they often have low affinity for target structures. Therefore, preferred ligands made from these components are engineered into dimeric, trimeric or tetrameric conjugates to increase functional affinity. See Tomlinson and Holliger, 2000; Carter, 2001; Hudson and Souriau, 2001; and Todorovska et al., 2001. Such conjugate structures may be created by chemical and/or genetic cross-links.

Bispecific ligands of the invention preferably are monospecific at each end, i.e., specific for a single component on minicells at one end and specific for a single component on target cells at the other end. The ligands may be multivalent at one or both ends, for example, in the form of so-called diabodies, triabodies and tetrabodies. See Hudson and Souriau, 2003. A diabody is a bivalent dimer formed by a non-covalent association of two scFvs, which yields two Fv binding sites. Likewise, a triabody results from the formation of a trivalent trimer of three scFvs, yielding three binding sites, and a tetrabody results from the formation of a tetravalent tetramer of four scFvs, yielding four binding sites.

Several humanized, human, and mouse monoclonal antibodies and fragments thereof that have specificity for receptors on mammalian cells have been approved for human therapeutic use, and the list is growing rapidly. See Hudson and Souriau, 2003. An example of such an antibody that can be used to form one arm of a bispecific ligand has specificity for HER2: Herceptin™; Trastuzumab.

Antibody variable regions also can be fused to a broad range of protein domains. Fusion to human immunoglobulin domains such as IgG1 CH3 both adds mass and promotes dimerization. See Hu et al., 1996. Fusion to human Ig hinge-Fc regions can add effector functions. Also, fusion to heterologous protein domains from multimeric proteins promotes multimerization. For example, fusion of a short scFv to short amphipathic helices has been used to produce miniantibodies. See Pack and Pluckthun, 1992. Domains from proteins that form heterodimers, such as fos/jun, can be used to produce bispecific molecules (Kostelny et al., 1992) and, alternately, homodimerization domains can be engineered to form heterodimers by engineering strategies such as "knobs into holes" (Ridgway et al., 1996). Finally, fusion protein partners can be selected that provide both multimerization as well as an additional function, e.g. streptavidin. See Dubel et al., 1995.

Minicells of the invention are anucleate forms of *E. coli* or other bacterial cells, engendered by a disturbance in the coordination, during binary fission, of cell division with DNA segregation. Prokaryotic chromosomal replication is linked to normal binary fission, which involves mid-cell septum formation. In *E. coli*, for example, mutation of min genes, such as minCD, can remove the inhibition of septum formation at the cell poles during cell division, resulting in production of a normal daughter cell and an anucleate minicell. See de Boer et al., 1992; Raskin & de Boer, 1999; Hu & Lutkenhaus, 1999; Harry, 2001. Minicells are distinct from other small vesicles that are generated and released spontaneously in certain situations and, in contrast to minicells, are not due to specific genetic rearrangements or episomal gene expression. For practicing the present invention, it is desirable for minicells to have intact cell walls ("intact minicells").

In addition to min operon mutations, anucleate minicells also are generated following a range of other genetic rearrangements or mutations that affect septum formation, for example in the divIVB1 in *B. subtilis*. See Reeve and Cornett, 1975; Levin et al., 1992. Minicells also can be formed following a perturbation in the levels of gene expression of proteins involved in cell division/chromosome segregation. For example, overexpression of minE leads to polar division and production of minicells. Similarly, chromosome-less minicells may result from defects in chromosome segregation for example the smc mutation in *Bacillus subtilis* (Britton et al., 1998), spoOJ deletion in *B. subtilis* (Ireton et al., 1994), mukB mutation in *E. coli* (Hiraga et al., 1989), and parC mutation in *E. coli* (Stewart and D'Ari, 1992). Gene products may be supplied in trans. When over-expressed from a high-copy number plasmid, for example, CafA may enhance the rate of cell division and/or inhibit chromosome partitioning after replication (Okada et al., 1994), resulting in formation of chained cells and anucleate minicells (Wachi et al., 1989; Okada et al., 1993). Minicells can be prepared from any bacterial cell of Gram-positive or Gram-negative origin.

Minicells of the invention contain a nucleic acid molecule that can be transcribed and/or translated to produce a desired product. For purposes of the present description, such nucleic acid molecules are categorized as "therapeutic nucleic acid molecules." In certain embodiments, the transcription and/or translation product functions to ameliorate or otherwise treat a disease or modify a trait in a cell, tissue or organ. Ordinarily, the therapeutic nucleic acid is found on a plasmid within the minicells.

The therapeutic nucleic acid molecule encodes a product, such as functional RNA (e.g., antisense, ribozyme, siRNA or shRNA) or a peptide, polypeptide or protein, the production of which is desired. For example, the genetic material of interest can encode a hormone, receptor, enzyme, or (poly) peptide of therapeutic value. Such methods can result in transient expression of non-integrated transferred DNA, extrachromosomal replication and expression of transferred replicons such as episomes, or integration of transferred genetic material into the genomic DNA of host cells.

Transcription or translation of a given therapeutic nucleic acid molecule may be useful in treating cancer or an acquired disease, such as AIDS, pneumonia, emphysema, or in correcting inborn errors of metabolism, such as cystic fibrosis. Transcription or translation of a therapeutic nucleic acid may also effect contraceptive sterilization, including contraceptive sterilization of feral animals. Allergen-mediated and infectious agent-mediated inflammatory disorders also can be countered by administering, via the present invention, a therapeutic nucleic acid molecule that, upon expression in a patient, affects immune response(s) associated with the allergen and infectious agent, respectively. A therapeutic nucleic acid molecule also may have an expression product, or there may be a downstream product of post-translational modification of the expression product, that reduces the immunologic sequalae related to transplantation or that helps facilitate tissue growth and regeneration.

A therapeutic nucleic acid molecule may be the normal counterpart of a gene that expresses a protein that functions abnormally or that is present in abnormal levels in a disease state, as is the case, for example, with the cystic fibrosis transmembrane conductance regulator in cystic fibrosis (Kerem et al., 1989; Riordan et al., 1989; Rommens et al., 1989), with β-globin in sickle-cell anemia, and with any of α-globin, β-globin and γ-globin in thalassemia. The therapeutic nucleic acid molecule can have an antisense RNA transcript or small interfering RNA, as mentioned above. Thus, an excess production of α-globin over β-globin which characterizes β-thalassemia can be ameliorated by gene therapy, in accordance with the present invention, using an intact minicell engineered to contain a plasmid incorporating a sequence that has an antisense RNA transcript vis-à-vis a target sequence of the α-globin mRNA.

In the treatment of cancer, a therapeutic nucleic acid molecule suitable for use according to the present invention could have a sequence that corresponds to or is derived from a gene that is associated with tumor suppression, such as the p53 gene, the retinoblastoma gene, and the gene encoding tumor necrosis factor. A wide variety of solid tumors—cancer, papillomas, and warts—should be treatable by this approach, pursuant to the invention. Representative cancers in this regard include colon carcinoma, prostate cancer, breast cancer, lung cancer, skin cancer, liver cancer, bone cancer, ovary cancer, pancreas cancer, brain cancer, head and neck cancer, and lymphoma. Illustrative papillomas are squamous cell papilloma, choroid plexus papilloma and laryngeal papilloma. Examples of wart conditions are genital warts, plantar warts, epidermodysplasia verruciformis, and malignant warts.

A therapeutic nucleic acid molecule for the present invention also can comprise a DNA segment coding for an enzyme that converts an inactive prodrug into one or more cytotoxic metabolites so that, upon in vivo introduction of the prodrug, the target cell in effect is compelled, perhaps with neighboring cells as well, to commit suicide. Preclinical and clinical applications of such a "suicide gene," which can be of non-human origin or human origin, are reviewed by Spencer (2000), Shangara et al. (2000) and Yazawa et al. (2002). Illustrative of suicide genes of non-human origin are those that code for HSV-thymidine kinase(tk), cytosine deaminase (CDA)+uracil phophoribosytransferase, xanthine-guanine phophoribosyl-transferase (GPT), nitroreductase (NTR), purine nucleoside phophrylase (PNP, DeoD), cytochrome P450 (CYP4B1), carboxypeptidase G2 (CPG2), and D-amino acid oxidase (DAAO), respectively. Human-origin suicide genes are exemplified by genes that encode carboxypeptidase A1 (CPA), deoxycytidine kinase (dCK), cytochrome P450 (CYP2B1,6), LNGFR/FKBP/Fas, FKBP/Caspases, and ER/p53, respectively.

A suicide-gene therapy could be applied to the treatment of AIDS. This strategy has been tested with suicide vectors that express a toxic gene product as soon as treated mammalian cells become infected by HIV-1. These vectors use the HIV-1 regulatory elements, Tat and/or Rev, to induce the expression of a toxic gene such as α-diphtheria toxin, cytosine deaminase, or interferon-a2 after infection by HIV-1. See Curiel et al., 1993; Dinges et al., 1995; Harrison et al., 1992a; Harrison et al., 1992b; Ragheb et al., 1999.

The therapeutic nucleic acid of the invention typically is contained on a plasmid within the minicell. The plasmid also may contain an additional nucleic acid segment that functions as a regulatory element, such as a promoter, a terminator, an enhancer or a signal sequence, and that is operably linked to the therapeutic nucleic acid segment. A suitable promoter can be tissue-specific or even tumor-specific, as the therapeutic context dictates.

A promoter is "tissue-specific" when it is activated preferentially in a given tissue and, hence, is effective in driving expression, in the target tissue, of an operably linked structural sequence. The category of tissue-specific promoters includes, for example: the hepatocyte-specific promoter for albumin and $_1$-antitrypsin, respectively; the elastase I gene control region, which is active in pancreatic acinar cells; the insulin gene control region, active in pancreatic beta cells; the mouse mammary tumor virus control region, which is active in testicular, breast, lymphoid and mast cells; the myelin basic protein gene control region, active in oligodendrocyte cells in the brain; and the gonadotropic releasing hormone gene control region, which is active in cells of the hypothalamus. See Frain et al. (1990), Ciliberto et al. (1985), Pinkert et al., (1987), Kelsey et al. (1987), Swift et al. (1984), MacDonald (1987), Hanahan, (1985), Leder et al. (1986), Readhead et al. (1987), and Mason et al. (1986).

There also are promoters that are expressed preferentially in certain tumor cells or in tumor cells per se, and that are useful for treating different cancers in accordance with the present invention. The class of promoters that are specific for cancer cells is illustrated by: the tyrosinase promoter, to target melanomas; the MUC1/Df3 promoter, to target breast carcinoma; the hybrid myoD enhancer/SV40 promoter, which targets expression to rhabdomyosarcoma (RMS); the carcinoembryonic antigen (CEA) promoter, which is specific for CEA-expressing cells such as colon cancer cells, and the hexokinase type II gene promoter, to target non-small cell lung carcinomas. See Hart (1996), Morton & Potter (1998), Kurane et al. (1998) and Katabi et al. (1999).

A signal sequence can be used, according to the present invention, to effect secretion of an expression product or localization of an expression product to a particular cellular compartment. Thus, a therapeutic polynucleotide molecule that is delivered via intact minicells may include a signal sequence, in proper reading frame, such that the expression product of interest is secreted by an engulfing cell or its progeny, thereby to influence surrounding cells, in keeping with the chosen treatment paradigm. Illustrative signal sequences include the haemolysin C-terminal secretion sequence, described in U.S. Pat. No. 5,143,830, the BAR1 secretion sequence, disclosed in U.S. Pat. No. 5,037,743, and the signal sequence portion of the zsig32 polypeptide, described in U.S. Pat. No. 6,025,197.

A plasmid within a minicell of the invention also may contain a reporter element. A reporter element confers on its recombinant host a readily detectable phenotype or characteristic, typically by encoding a polypeptide, not otherwise produced by the host, that can be detected, upon expression, by histological or in situ analysis, such as by in vivo imaging techniques. For example, a reporter element delivered by an intact minicell, according to the present invention, could code for a protein that produces, in the engulfing host cell, a colorimetric or fluorometric change that is detectable by in situ analysis and that is a quantitative or semi-quantitative function of transcriptional activation. Illustrative of these proteins are esterases, phosphatases, proteases and other enzymes, the activity of which generates a detectable chromophore or fluorophore.

Preferred examples are E. coli β-galactosidase, which effects a color change via cleavage of an indigogenic substrate, indolyl-β-D-galactoside, and a luciferase, which oxidizes a long-chain aldehyde (bacterial luciferase) or a heterocyclic carboxylic acid (luciferin), with the concomitant release of light. Also useful in this context is a reporter element that encodes the green fluorescent protein (GFP) of the jellyfish, Aequorea victoria, as described by Prasher et al. (1995). The field of GFP-related technology is illustrated by two published PCT applications, WO 095/21191 (discloses a polynucleotide sequence encoding a 238 amino-acid GFP apoprotein, containing a chromophore formed from amino acids 65 through 67) and WO 095/21191 (discloses a modification of the cDNA for the apopeptide of A. victoria GFP, providing a peptide having altered fluorescent properties), and by a report of Heim et al. (1994) of a mutant GFP, characterized by a 4-to-6-fold improvement in excitation amplitude.

Another type of a reporter element is associated with an expression product that renders the recombinant minicell resistant to a toxin. For instance, the neo gene protects a host against toxic levels of the antibiotic G418, while a gene encoding dihydrofolate reductase confers resistance to methotrexate, and the chloramphenicol acetyltransferase (CAT) gene bestows resistance to chloramphenicol.

Other genes for use as a reporter element include those that can transform a host minicell to express distinguishing cell-surface antigens, e.g., viral envelope proteins such as HIV gp120 or herpes gD, which are readily detectable by immunoassays.

Target cells of the invention include any cell into which an exogenous nucleic acid molecule is to be introduced. ("Introduced," when used in reference to an exogenous nucleic acid molecule, means that the nucleic acid molecule carried within a minicell is delivered to the target cell.) Desirable target cells are characterized by expression of a cell surface receptor that, upon binding of a ligand, facilitates endocytosis. Preferred target cells are non-phagocytic, meaning that the cells ordinarily do not ingest bacterial particles, and are mammalian.

Methods and compositions of the invention can be used to deliver a range of nucleic acid molecules, which can be cDNA as well as genomic DNA or RNA, and can be in the sense or the anti-sense orientation. The nucleic acid molecule present in a minicell, pursuant to the present invention, can take the form of a plasmid, expression vector, or other genetic construct, but is not genomic DNA originating from the bacterial cell that gave rise to the minicell. Suitable for use in the present invention is any desired DNA or RNA sequence from a eukaryotic, prokaryotic, or synthetic source which may be placed under the translational and transcriptional control of a eukaryotic gene expression promoter, or which may be expressed in the mammalian cell using trans-activating factors from the host cell.

Methods of the invention may be performed in vivo or ex vivo. In an ex vivo procedure, for example, target cells may be removed from a subject, such as by biopsy. An appropriate ligand may be selected based on knowledge of a cell surface receptor that is expressed by the target cells. The gene(s) to be delivered to the target cells are cloned into an appropriate episomal carrier DNA, for example a plasmid, and transferred into parent bacterial cells from which the intact minicells are to be derived. Processes for obtaining minicells are well known in the art, as described in PCT/IB02/04632. Minicells carrying the recombinant DNA are then purified by procedures known in the art and described in PCT/IB02/04632. The bispecific ligand is then bound to the recombinant purified minicells, for example by in vitro incubation in suitable medium, and excess ligand is washed away from the ligand-loaded minicells. The composition comprising purified intact minicells and the bispecific ligand, attached to the minicells via one arm that has specificity for a minicell surface component, is then brought into contact with target cells either in vitro, for example, in tissue culture (as described in Example 1, 2 and 3), or in vivo (as described in example 4).

Thus, the invention includes a method for performing ex vivo gene therapy into desired non-phagocytic mammalian cells that are normally refractory to minicell-mediated gene therapy. Depending upon the target cells and therapeutic nucleic acid, the present invention can be used in treatment of various conditions and diseases, to increase expression of a desired protein, to inhibit expression or function of a gene product, and so forth. For instance, transcription or translation of a given therapeutic nucleic acid molecule may be useful in treating cancer or an acquired disease, such as AIDS, pneumonia, emphysema, or in correcting inborn errors of metabolism, such as cystic fibrosis. Transcription or translation of a therapeutic nucleic acid may also effect contraceptive sterilization, including contraceptive sterilization of feral animals. Allergen-mediated and infectious agent-mediated inflammatory disorders also can be countered by administering, via the present invention, a therapeutic nucleic acid molecule that, upon expression in a patient, affects immune response(s) associated with the allergen and infectious agent, respectively. A therapeutic nucleic acid molecule also may have an expression product, or there may be a downstream product of post-translational modification of the expression product, that reduces the immunologic sequalae related to transplantation or that helps facilitate tissue growth and regeneration.

The invention also relates to the transfer of nucleic acids into selected cell types in vitro. Such transfers are useful for a variety of purposes, such as to create a cell that can produce large quantities of a selected protein, which can then be harvested.

In a related aspect, the invention provides a composition of matter useful for introducing exogenous nucleic acid molecules into target non-phagocytic mammalian cells with high efficiency. The composition comprises (i) a bacterially derived minicell and (ii) a bispecific ligand. The minicell and ligand may be any of those described herein. Thus, the minicell contains a therapeutic nucleic acid molecule and the bispecific ligand preferably is capable of binding to a surface component of the minicell and to a surface component of a target mammalian cell.

A composition consisting essentially of recombinant minicells and bispecific ligands of the present invention (that is, a composition that includes such minicells and ligands with other constituents that do not interfere unduly with the DNA-delivering quality of the composition) can be formulated in conventional manner, using one or more physiologically acceptable carriers or excipients. Formulations for injection may be presented in unit dosage form, e.g., in ampules or vials, or in multi-dose containers, with or without an added preservative. The formulation can be a solution, a suspension, or an emulsion in oily or aqueous vehicles, and may contain formulatory agents, such as suspending, stabilizing and/or dispersing agents. A suitable solution is isotonic with the blood of the recipient and is illustrated by saline, Ringer's solution, and dextrose solution. Alternatively, compositions may be in lyophilized powder form, for reconstitution with a suitable vehicle, e.g., sterile, pyrogen-free water or physiological saline. The compositions also may be formulated as a depot preparation. Such long-acting formulations may be administered by implantation (for example, subcutaneously or intramuscularly) or by intramuscular injection.

A composition of the present invention can be administered via various routes and to various sites in a mammalian body, to achieve the therapeutic effect(s) desired, either locally or systemically. Delivery may be accomplished, for example, by oral administration, by application of the formulation to a body cavity, by inhalation or insufflation, or by parenteral, intramuscular, intravenous, intraportal, intrahepatic, peritoneal, subcutaneous, intratumoral, or intradermal administration. The mode and site of administration is dependent on the location of the target cells. For example, cystic-fibrotic cells may be efficiently targeted by inhaled delivery of the targeted recombinant minicells. Similarly, tumor metastasis may be more efficiently treated via intravenous delivery of targeted recombinant minicells. Primary ovarian cancer may be treated via intraperitoneal delivery of targeted recombinant minicells.

The following examples are intended to illustrate and provide a more complete understanding of the invention without limiting the invention to the examples provided.

Example 1. Highly Efficient Binding and Receptor-Mediated Internalization of Bispecific Antibody-Targeted Minicells into Non-Phagocytic Human Prostate Carcinoma Cells This experiment demonstrates that a bispecific antibody with Fab fragments carrying anti-*S. typhimurium* LPS and anti-androgen receptor binding specificities can enable binding and receptor-mediated internalization of *S. typhimurium*-derived minicells into prostate carcinoma cells that are known to over-express the androgen receptor on the cell surface.

*S. typhimurium* minCDE-mutant strain generated previously (patent application, PCT/IB02/04632) was transformed with recombinant plasmid pORF5-HSV1tk::Sh ble (Invivogen, San Diego, Calif., USA). The plasmid is a mammalian gene expression vector that expresses the HSV1tk::Sh ble fusion gene under the control of the EF-1/eIF4g hybrid promoter. The HSV1tk is a suicide gene from Herpes simplex serotype 1 virus (HSV1) and encodes an enzyme, thymidine kinase, that can convert prodrug guanosine analog ganciclovir (GCV) to ganciclovir-monophosphate (GCV-MP). The latter is then converted to the diphosphate and triphosphate forms by endogenous kinases. GCV-triphosphate lacks the 3' OH on the deoxyribose as well as the bond between the 2' and 3' carbons which are necessary for DNA chain elongation. As a result, GCV-triphosphate integration causes premature DNA chain termination and leads to apoptosis. Expression of HSV1tk therefore sensitizes transfected mammalian cells to ganciclovir and is one of the most widely used single suicide strategies for cancer gene therapy (Singhal and Kaiser, 1998). As a control, a plasmid was constructed where HSVtk::Sh ble gene fusion was deleted by cleaving plasmid pORF5-HSV1tk::Sh ble with restriction enzymes NcoI and NheI, blunt-ending the sites with T4 DNA polymerase and religating the plasmid. The NcoI and NheI sites are unique in plasmid pORF5-HSV1tk::Sh ble and flank the HSV1tk::Sh ble gene fusion.

The resulting plasmid designated pORF5-HSV1tk– was also transformed in *S. typhimurium* minCDE-mutant strain.

Recombinant minicells carrying the plasmids were purified using the gradient centrifugation/filamentation/filtration/endotoxin removal procedure described in international patent application PCT/IB02/04632.

The bispecific antibody was constructed by linking anti-*S. typhimurium* lipopolysaccharide (Biodesign, Saco, Me., USA) and anti-androgen receptor mouse monoclonal antibodies (IgG; Abcam, Cambridge, UK) to purified recombinant protein A/G via the Fc fragments of each monoclonal antibody and in brief the procedure was as follows.

Purified recombinant protein A/G (Pierce Biotechnology, Rockford, Ill., USA) was diluted to a final concentration of 100 µg/ml in Immunopure binding buffer (Pierce Biotechnology) and 0.5 ml of the solution was incubated overnight at 4° C. with a premixed solution containing 20 µg/ml each of anti-*S. typhimurium* LPS (Research Diagnostics Inc., Flanders, N.J., USA) and anti-human androgen receptor (Abcam, Cambridge, UK) monoclonal antibodies. The excess antibodies unbound to protein A/G were then removed as follows. Dynabeads® Protein G solution (Dynabeads® [2.8 µm] coated with recombinant Protein G covalently coupled to the surface of the magnetic particles; Dynal Biotech, Oslo, Norway) was mixed gently and 100 µl of the solution was transferred into an eppendorf centrifuge tube. The tube was placed in the Dynal MPC-S (Magnetic Particle Concentrator, type S) to immobilize the beads and the supernatant was discarded. The beads were resuspended in 0.5 ml of washing solution containing 0.1M Na-phosphate buffer (pH 5.0). The bead immobilization and washing steps were repeated three times. The solution containing protein A/G-bispecific antibody complex was added to the beads and incubated with gentle mixing at room temperature for 40 min. The tube was placed on the MPC-S stand to immobilize the beads and the protein A/G-bispecific antibody complex was removed with a pipette. This step removed the unbound excess monoclonal antibodies from the solution and provided a solution that carried the bispecific antibody linked to protein A/G via their Fc fragments.

$10^{10}$ recombinant minicells were incubated with the protein A/G-bispecific antibody for 1 hr at room temperature to coat the minicells with the antibody via its anti-LPS Fab region.

Prostate carcinoma cells, LNCaP (ATCC, Rockville, Md., USA) were grown to full confluency in T-75 flasks in RPMI 1640 medium supplemented with 10% FCS and antibiotics. The cells were passaged in T-25 flasks at 50% confluency. After overnight attachment, the culture medium was refreshed and to one flask was added $10^7$ recombinant minicells carrying plasmid pORF5-HSV1tk::Sh ble (non-targeted recombinant minicells) and to another flask was added $10^7$ of the same minicells but carrying cell surface attached bispecific antibody (targeted recombinant minicells). The ratio of minicells to prostate carcinoma cells was 100:1. The transfected cells were incubated in an incubator under 5% $CO_2$ and 37° C. for 16, 24 and 36 hrs followed by four washes (5 ml per wash) with fresh 1× Dulbecco's medium with gentle shaking. All cells were trypsinized and then passaged on 13 mm coverslips in 24 well plate (each time point in triplicate), with cell numbers in sub-confluency.

Figure 1:
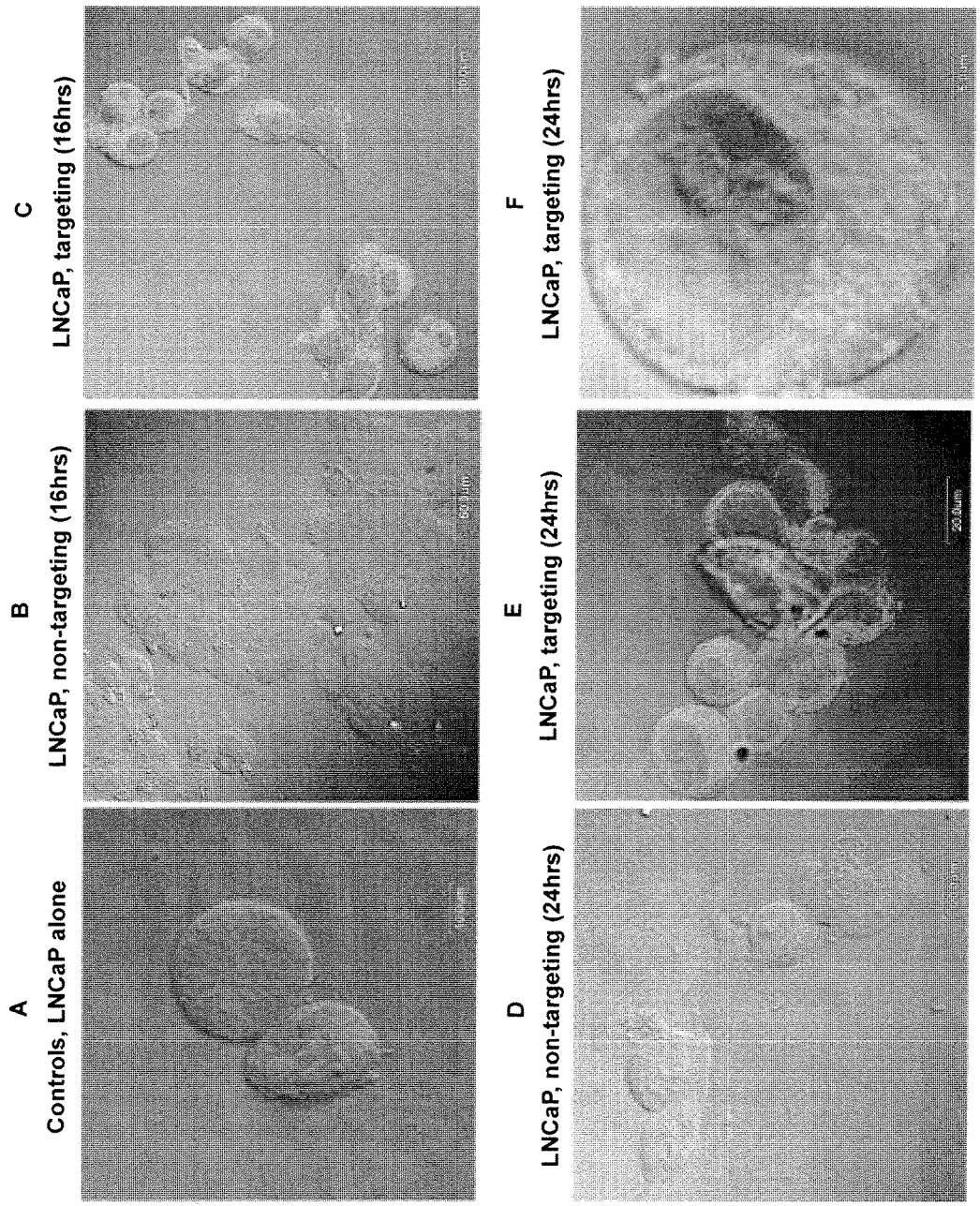
FIG. 1 shows efficient internalization of human androgen receptor-targeted recombinant minicells, in contrast to non-targeted minicells, into human prostate carcinoma LNCaP cells. The procedures were performed as described in Example 1 and the results were visualized by confocal microscopy Immunofluorescence staining was performed for all shown images with anti-S. typhimurium LPS specific monoclonal antibody, followed by Alexa Fluor 594-conjugated goat anti-mouse IgG (H+L) antibody. Each figure is shown as an overlap of Differential Interference Contrast (DIC) and red fluorescence images. (A) Control LNCaP cells not transfected with minicells. No red fluorescence was observed following staining for S. typhimurium LPS. (B) LNCaP cells transfected with non-targeted minicells and stained after 16 hr co-incubation. Very few background red fluorescence dots were observed. (C) LNCaP cells transfected with targeted minicells and stained after 16 hrs. Most cells showed red fluorescence in the cytoplasm, revealed in the black-and-white image as light grey. (D) LNCaP cells transfected with non-targeted minicells and stained after 24 hr co-incubation. Very few background red fluorescence dots were observed. (E) LNCaP cells transfected with targeted minicells and stained after 24 hrs. The result showed intense red fluorescence in the cytoplasm of most cells (light grey in the image), (F) Same as (E) but at a higher magnification to show a single transfected cell. Almost all the cytoplasm fluoresced red (light grey). Scale bars are shown for each image.

The cells on coverslips were fixed with 4% paraformaldehyde for 30 mins and blocked with 5% normal goat serum overnight followed by staining with anti-*S. typhimurium* LPS (1:200; Biodesign, Saco, Me., USA) monoclonal antibody. The antibody binding was revealed with goat anti-mouse IgG conjugated with Alexa Fluor 594 (1:1000, red fluorescence; excitation 590 nm and emission 617 nm; Molecular Probes, Eugene, Oreg., USA) and viewed by fluorescence confocal microscopy (Fluoview, Olympus America, Melville, N.Y., USA). Fluorescence and Differential Image Contrast (DIC) images were collected and overlaid as shown in FIG. 1.

The results showed that non-targeted recombinant minicells did not specifically adhere to or get internalized in the LNCaP prostate carcinoma cells at any of the time points analyzed (FIGS. 1B and 1D) and cells appeared the same as control non-transfected cells. All fields analyzed revealed minor background red fluorescence. In contrast, the targeted recombinant minicells were found to strongly adhere to the LNCaP cells presumably via binding of the targeting bispecific antibody to the cell surface androgen receptor. Additionally, at the 16 hr and 24 hr incubation time points, most LNCaP cells showed intense red fluorescence within the cytoplasm of the cells (FIGS. 1C, 1E and 1F) indicating that the minicells had been internalized via receptor-mediated endocytosis.

This result suggested that the minicells carrying surface-attached bispecific antibody mediated highly efficient binding of the minicells to the cell surface receptor found on a mammalian cell (androgen receptor in the above example) and that the adherent minicells were rapidly internalized by the non-phagocytic mammalian cell (prostate carcinoma cell in the above example).

Example 2. Highly Efficient Binding and Receptor-Mediated Internalization of Bispecific Antibody-Targeted Minicells into Non-Phagocytic Human Breast Adenocarcinoma Cells Example 1 demonstrated that a bispecific antibody with anti-LPS (minicell specificity) and anti-androgen receptor binding specificity can efficiently enable strong binding to the androgen receptor on a non-phagocytic mammalian cell, the prostate carcinoma cell. Additionally, the results demonstrated that the receptor binding triggered receptor-mediated endocytosis of the recombinant minicells at a high efficiency. This example demonstrates that the above-observed phenomenon is generalized and that the invention and discover are applicable to a range of different endocytosis-competent receptors, on different non-phagocytic mammalian cells.

More specifically, this experiment shows that human breast adenocarcinoma cells (MDA-MB-468, ATCC; human mammary epithelial cells; non-phagocytic) can be targeted via a bispecific antibody carrying Fab fragments with anti-*S. typhimurium* LPS (minicell surface binding specificity) and anti-epidermal growth factor receptor (EGFR) binding specificity. The cell line MDA-MB-468 cells were grown in tissue culture as described for prostate carcinoma cells in example 1. The bispecific antibody was constructed as described in Example 1, except that the anti-androgen receptor monoclonal antibody was replaced with anti-EGFR monoclonal antibody (Oncogene Research Products, Cambridge, Mass., USA). Targeted and non-targeted recombinant minicells were generated and used to transfect the MDA-MB-468 cells and the cells were stained for *S. typhimurium* LPS (minicells) at time intervals of 16 hours, 24 hours, and 36 hours as described above for prostate carcinoma cells.

Figure 2:
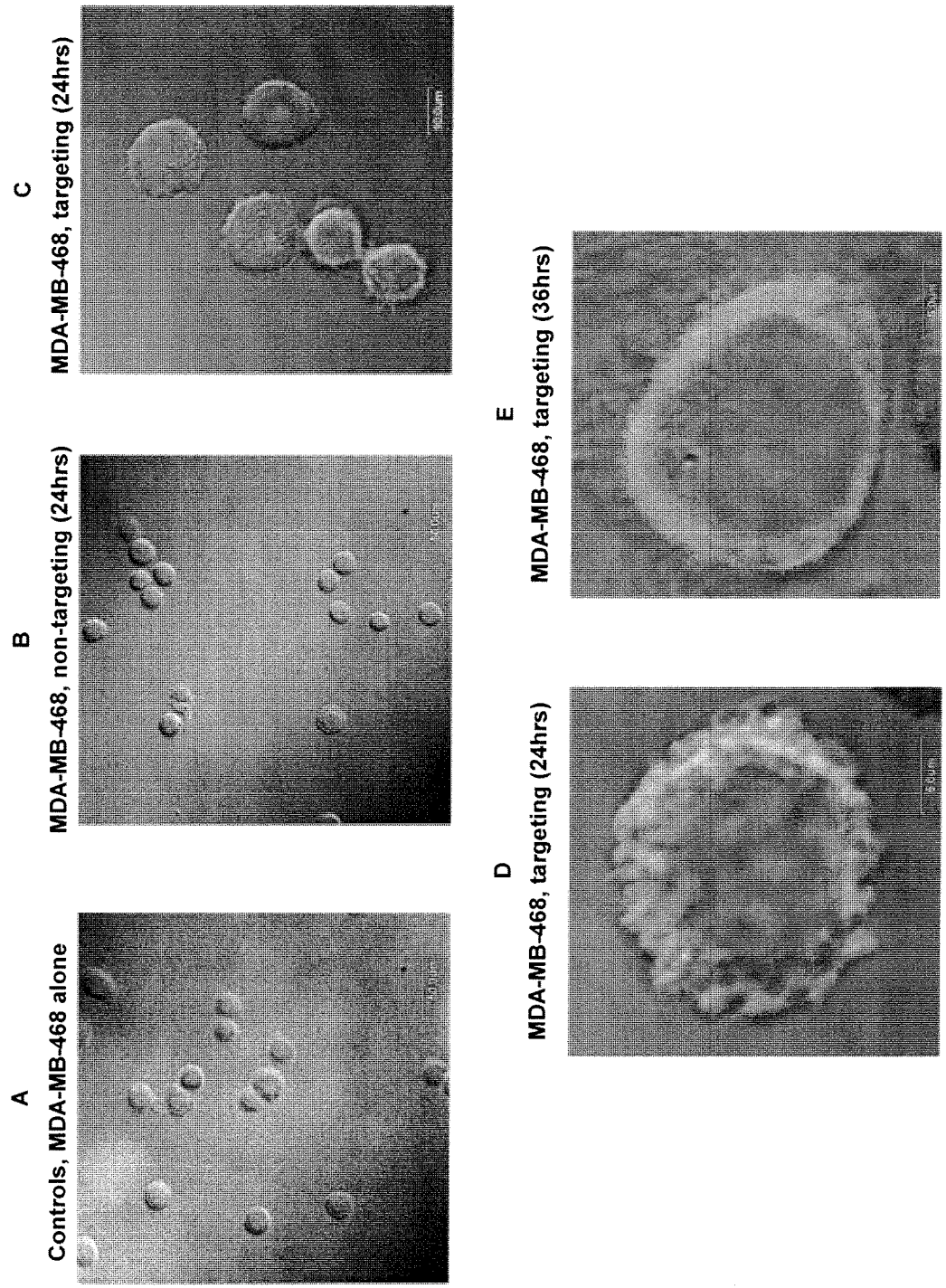
FIG. 2 shows efficient internalization of EGF receptor-targeted recombinant minicells, versus non-targeted minicells, into human breast cancer MDA-MB-468 cells. The procedures were performed as described in Example 2 and the results were visualized by confocal microscopy Immunofluorescence staining was performed for all shown images with anti-S. typhimurium LPS specific monoclonal antibody, followed by Alexa Fluor 594-conjugated goat anti-mouse IgG (H+L) antibody. Each image is shown as an overlap of DIC and red fluorescence images. (A) Control MDA-MB-468 cells not transfected with minicells. No red fluorescence was observed following staining for S. typhimurium LPS. (B) MDA-MB-468 cells transfected with non-targeted minicells and stained after 24 hr co-incubation. Very few background red fluorescence dots were observed. (C) MDA-MB-468 cells transfected with targeted minicells and stained after 24 hrs. Most cells showed red fluorescence on the surface and some in the cytoplasm (light grey area in the black-white image). (D) Same as (C) but at a higher magnification to reveal a single cell. The result was the same as for (C). (E) Same as (D) except cells were stained after 36 hrs. The result showed intense red fluorescence in the cytoplasm of most cells (light grey in the image). Scale bars are shown for each image.

The results revealed (FIG. 2) that control cells and cells treated with non-targeted minicells exhibited only minor background red fluorescence at all the time points (FIGS. 2A and 2B), suggesting that the minicells were unable to adhere to and transfect the non-phagocytic mammalian cells. In contrast, the cells treated with targeted minicells exhibited strong red fluorescence in the cytoplasm after 24 hrs incubation and the fluorescence increased to cover more of the cytoplasm after 36 hrs (FIGS. 2C-E). This suggested that the bispecific antibody enabled the strong binding of the minicells to the EGF receptor on the surface of MDA-MB-468 cells and that the binding triggered receptor mediated endocytosis of the minicells.

Example 3. Highly Efficient Binding and Receptor-Mediated Internalization of Bispecific Antibody-Targeted Minicells into Non-Phagocytic Human Ovarian Carcinoma Cells Examples 1 and 2 demonstrated that a bispecific antibody with anti-LPS (minicell specificity) and either anti-androgen receptor binding specificity or anti-EGFR specificity can efficiently enable strong binding to the androgen receptor or EGFR on a non-phagocytic prostate carcinoma cells and breast carcinoma cells respectively. Additionally, the results demonstrated that the receptor binding triggered receptor-mediated endocytosis of the recombinant minicells at a high efficiency. This example further demonstrates the general applicability of the invention and discovery.

Accordingly, this experiment demonstrates that human ovarian carcinoma cells (SKOV-3, ATCC; epithelial cells; non-phagocytic) can be targeted via a bispecific antibody carrying Fab fragments with anti-*S. typhimurium* LPS (minicell surface binding specificity) and mouse anti-human Her2/neu receptor (Serotec Inc., Raleigh, N.C., USA) binding specificity. SKOV-3 cells are known to overexpress the Her2 receptor (Salomon et al., 1995). The experiment was performed as described in Examples 1 and 2, and the samples were stained for anti-LPS (red fluorescence) as before.

Figure 3:
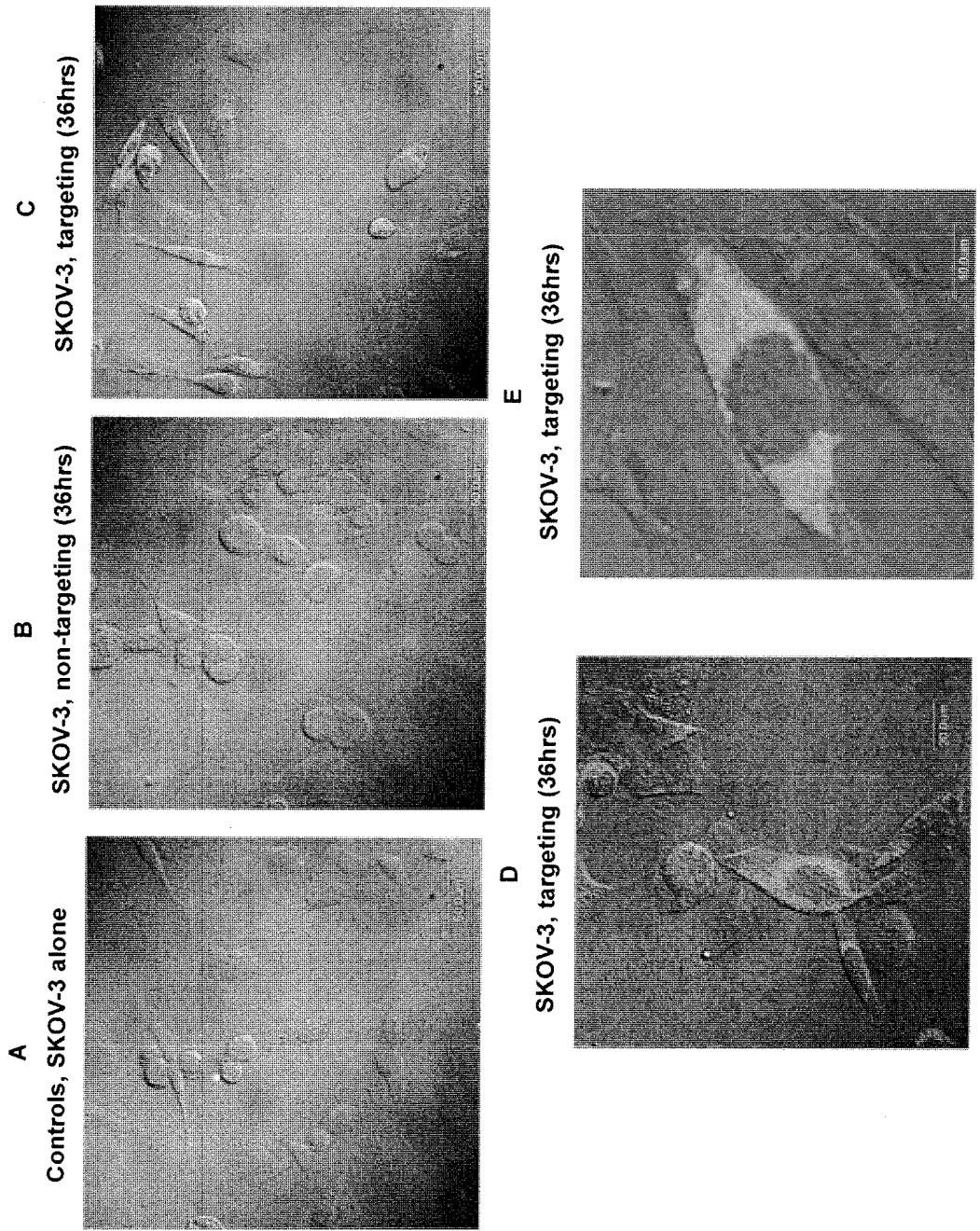
FIG. 3 shows efficient internalization of Her2/neu receptor-targeted recombinant minicells, versus non-targeted minicells, into human ovarian cancer SKOV-3 cells. The procedures were performed as described in Example 3 and the results were visualized by confocal microscopy Immunofluorescence staining was performed for all shown images with anti-S. typhimurium LPS specific monoclonal antibody, followed by Alexa Fluor 594-conjugated goat anti-mouse IgG (H+L) antibody. Each image is shown as an overlap of DIC and red fluorescence images. (A) Control SKOV-3 cells not transfected with minicells. No red fluorescence was observed following staining for S. typhimurium LPS. (B) SKOV-3 cells transfected with non-targeted minicells and stained after 36 hr co-incubation. Very few background red fluorescence dots were observed. (C) SKOV-3 cells transfected with targeted minicells and stained after 36 hrs. Most cells showed red fluorescence in the cytoplasm (light grey area in the black-white image). (D) Same as (C) but at a higher magnification. The result was the same as for (C). (E) Same as (C) but higher magnification to show a few cells.

The results (FIG. 3) were similar to those obtained in examples 1 and 2. The control SKOV-3 cells and those treated with non-targeted minicells, showed only minor background red fluorescence.

Example 4. Highly Efficient Gene Delivery to Non-Phagocytic Mammalian Cells Via Bispecific Antibody Mediated Targeting of Recombinant Minicells The above experiments demonstrated highly efficient attachment of minicells to non-phagocytic mammalian cells, e.g., human epithelial cancer cells. This example demonstrates that non-phagocytic mammalian cells have an efficient intracellular mechanism for degrading endocytosed particles that are as large as minicells (400 nm diameter). This example also shows that plasmid DNA packaged in minicells can escape the intracellular degradative processes, escape the endosomal membranes, enter the cytoplasm, enter the cell nucleus and become recombinantly expressed. Indeed, minicells can efficiently deliver genes to non-phagocytic cells, indicating that applications of the invention are useful in vitro transfection tools.

Human breast cancer cells (MDA-MB-468) were incubated with control non-targeted, non-specifically targeted and experimental EGFR-targeted minicells carrying a plasmid that encodes the viral Hepatitis B Surface antigen (HbsAg; Aldevron, USA). Non-specifically targeted BsAb was constructed using anti-cytomegalovirus (CMV) monoclonal antibody and anti-*S. typhimurium* LPS Mab. At time intervals of 4 hours, 8 hours, 16 hours, 24 hours and 36 hours, the cells were washed and fixed with 4% paraformaldehyde and blocked with 5% normal goat serum/2% BSA. The membrane permeability was increased with 1% Triton X-100 in PBS and cells were treated with anti-HbsAg MAb (Aldevron, diluted in 1:100) followed by Alexa Fluor 594-conjugated goat anti-mouse IgG (Molecular probes, diluted in 1:1000). The HbSAg protein expressing cells were analyzed by Confocal Microscopy. To determine the efficiency of gene delivery, the cells were analyzed by Flow Cytometry. For FACS analysis, the cells were treated with anti-HBsAg MAb followed by Phycoerythrin (PE)-conjugated goat anti-mouse IgG instead of Alexa Fluor 594 because FACS analysis is more sensitive to PE compared to Alexa Fluor 594.

The results revealed that only the EGFR-targeted minicells gave a gene delivery efficiency of greater than 95% (FIG. 4Aiv). The recombinant protein expression (cells fluorescing bright red; FIG. 4Bii-iii) was observed 16 hours post-transfection (FIG. 4Aiv) and at subsequent time points, suggesting significant levels of recombinant protein per cell. All control cells showed only background red fluorescence dots (FIG. 4Bi).

These results were surprising because it was not known that non-phagocytic cells would carry such an efficient intracellular mechanism for degrading endocytosed particles that are as large as minicells (400 nm diameter) and that carry a rigid biological membrane. Additionally, an unexpectedly high level of efficiency (greater than 95%) of gene delivery to non-phagocytic mammalian cells was observed. These results indicate that applications of the invention are useful in vitro transfection tools. No currently available tools achieve such a high degree of specific gene delivery to non-phagocytic mammalian cells.

Example 5. Bispecific Antibody-Mediated Targeting of Minicells to Human Breast Cancer Xenografts in Female Athymic Nude Mice This example demonstrates that targeted recombinant minicells carrying a plasmid encoding HSVtk gene can effect regression of human breast cancer cell tumor xenografts established in 6 week old female athymic nude mice.

The bispecific antibody was constructed as described in Example 1, except that instead of the anti-androgen receptor monoclonal antibody, the anti-epidermal growth factor receptor (anti-EGFR) monoclonal antibody (Oncogene Research Products, Cambridge, Mass., USA) was used. This was because the xenografted cells were human breast cancer cells MDA-MB-468 that are known to overexpress the EGF receptor on the cell surface. The mice were purchased from Animal Resources Centre, Perth, Wash., and all animal experiments were performed in compliance with the guide of care and use of laboratory animals and with Animal Ethics Committee approval. The experiments were performed in the NSW Agriculture accredited small animal facility at EnGeneIC Pty Ltd (Sydney, NSW, Australia). MDA-MB-468 human breast cancer cells were cultured as described in example 2 and $1.5 \times 10^6$ cells in 50 μL serum-free media together with 50 μL growth factor reduced matrigel (BD Biosciences, Franklin Lakes, N.J., USA) were injected subcutaneously between the shoulder blades of each mouse using a 23-gauge needle. The tumors were measured twice a week using an electronic digital caliper (Mitutoyo, Japan, precision to 0.001) and tumor volume was calculated using the formula, length (mm)×width$^2$ (mm)×0.5=volume (mm$^3$) 21 days post-implantation the tumors reached volumes between 50 mm$^3$ and 80 mm$^3$, and mice were randomized to six different groups of 12 per group.

The experiment was designed as follows. Group 1 (control) received no treatment. Group 2 (control) received non-targeted recombinant minicells that carried plasmid pORF5-HSV1tk::Sh ble (designated M-HSVtk) on days 21, 28 and 35. The mice also received GCV on days 25, 26, 32, 33, 39 and 40, i.e., two doses of GCV on successive days. This group was designed to determine if non-targeted minicells could deliver the suicide gene to the tumor cells and affect tumor regression following GCV treatment. Group 3 (control) was designed to determine if treatment with targeted recombinant minicells carrying plasmid pORF5-HSV1tk::Sh ble in the absence of GCV had any effect on tumor regression. Therefore, Group 3 mice received targeted recombinant minicells carrying plasmid pORF5-HSV1tk::Sh ble (designated TM-HSVtk) on the same days as for group 2 but received no GCV treatment. Group 4 (control) was designed to determine if the bispecific antibody in the absence of recombinant minicells had any effect on tumor regression. Therefore, these mice received the bispecific antibody on the same days that recombinant targeted or non-targeted minicells were given, i.e., days 21, 28 and 35. The antibody treatment was followed by GCV treatment on the same days as for group 2. Group 5 (experimental) was designed to determine if the targeted recombinant minicells carrying plasmid pORF5-HSV1tk::Sh ble could effectively deliver the plasmid to the xenografted tumor cells and if tumor regression could be observed following treatment of the mice with a single dose of GCV after each minicell dose. Therefore, group 5 received targeted recombinant minicells on the same days as for group 3 followed by GCV treatment on days 25, 33 and 39. Group 6 (experimental) was the same as group 5 but received two doses of GCV on successive days, as for groups 2 and 4.

Mice receiving the respective minicells were injected intratumorally with $10^8$ minicells resuspended in 30 ul of sterile physiological saline. Gene targeting experiments in vitro in MDA-MB-468 cells had revealed that the minicell delivered plasmid expressed the HSVtk enzyme after at least 48 hrs post-transfection with the targeted recombinant minicells. Therefore, groups 2, 4, 5 and 6 were given GCV after 3 to 4 days post-minicell inoculation to allow the transfected tumor xenograft cells to sufficiently express the HSVtk enzyme to be responsive to GCV. GCV was administered intraperitoneally at a concentration of 100 mg/kg of mouse weight.

FIG. 5 shows the progression in tumor volume over the course of the experiment. The results revealed that only targeted recombinant minicells (Groups 5 and 6) were able to successfully deliver the HSV1tk gene encoding plasmid to the xenografted tumor cells. The tumor volumes in these two groups did not increase in size and remained stable throughout the course of the experiment. In contrast, the tumor volumes rapidly increased in the four control groups (Groups 1-4). Interestingly, group 2 mice also showed no evidence of tumor regression, suggesting the non-targeted recombinant minicells could not transfect the human breast cancer cells and achieve a clinically significant outcome. Statistical analysis of the data using One-way ANOVA showed that experimental groups (5 and 6) were highly significant compared to the control groups 1 to 4 (p=0.001). This result is a first demonstration of targeted in vivo gene delivery to non-phagocytic mammalian cells mediated by bacterially derived intact recombinant minicells. It also demonstrates a role for receptor-mediated endocytosis of the minicells in achieving highly significant gene delivery to these non-phagocytic mammalian cells (compare group 2 with groups 5 and 6).

The results of this experiment show the significance of the inventive compositions and methods for targeting minicells to desired mammalian cells in vivo. The results also demonstrate the potential for clinical application of targeted minicells, particularly in the development of cancer therapeutics.

Example 6. Suicide Plasmid Carrying Minicells Targeted to Over-Expressed EGF Receptor on Human Breast Cancer Xenografts, Effectively Regress the Tumor in Nude Mice The above-described xenograft studies were performed by intratumoral (i.t.) injection of minicells. To evaluate the potential for targeting minicells to non-phagocytic (human cancer cell) cell surface receptors via systemic delivery and achieving tumor stabilisation/regression in vivo, another xenograft study was designed where the minicells were injected intravenously.

Accordingly, recombinant minicells carrying plasmid pORF5-HSV1tk::Sh ble (HSV1tk) were constructed and purified. The minicells were targeted to the human EGFR that was shown to be over-expressed on human breast cancer cells MDA-MB-468. This was accomplished by constructing a bispecific antibody with anti-human EGFR and anti-S. typhimurium LPS specificities and attaching the BsAb to the minicell surface, as described in Example 1. The xenografts were established subcutaneously (s.c.) between the shoulder blades of nude mice (n=11 per group), and the experimental and control minicells were administered i.v. in the tail vein on the days shown (FIG. 6). Groups 2, 4, 6 and 7 also received GCV (i.p.) on the days shown.

The results revealed a significant stabilization/regression of the established tumors only in mice treated with EGFR-targeted minicells$_{HSVtk}$. Both minicell doses $10^8$ or $10^9$ per dose were equally effective, indicating that the targeting methodology is highly efficient and enhances the therapeutic index, making vector concentration less of a limiting factor. Statistical analysis of the data using One-way ANOVA showed that results in the experimental groups (6 and 7) were highly significant compared to the control groups 1 to 5 (p=0.0001). This data showed that the minicell targeting technology was highly effective at homing the minicells to the tumor mass, even when injected at a site distant from the tumor. The data also showed that systemic delivery of targeted minicells did not cause any overt signs of toxicity to the mice. Throughout the study, there were no overt signs of toxicity such as fever, lethargy, loss of appetite, weight loss or death.

Example 7. Suicide Plasmid-Carrying Minicells Targeted to Under-Expressed HER2/Neu Receptor on Human Breast Cancer Xenografts, Effectively Regress the Tumor in Nude Mice The above-described in vivo results indicated that minicells could be effectively targeted to over-expressed receptors on diseased cells, such as cancer cells. This example shows the efficacy of a minicell vector when targeted to a poorly expressed receptor on the cancer cell surface. In conventional approaches targeting poorly expressed receptors is a serious hurdle to the development of antibody-based therapeutics, particularly for cancer treatment, because many cancer cells do not over-express targeted receptors.

For example, the HER2/neu receptor is over-expressed in fewer than 20% of breast cancer patients.

Accordingly, a xenograft study was designed where the minicell$_{HSVtk}$ vector was targeted to the HER2/neu receptor that is known to be poorly expressed on the MDA-MB-468 breast cancer cells. Experimental and control groups (FIG. 7) were the same as in Example 6, except that one more experimental group was included (G8) where the HER2/neu-targeted minicell$_{HSVtk}$ was injected intratumoraly. The results (FIG. 7) showed that, although the HER2/neu receptor is poorly expressed, the experimental treatments were just as effective in achieving tumor stabilisation/regression as in the case of Example 6, where the minicell$_{HSVtk}$ vector was targeted to the over-expressed EGF receptor. The same number of doses (3×) of targetedminicell$_{HSVtk}$ were required to achieve the result. In this experiment, once the residual tumors began to grow between days 53 and 81, a fourth dose of HER2/neu-targeted minicell$_{HSVtk}$ was administered, resulting in a rapid drop in tumor volumes in groups 6 and 7. Statistical analysis of the data, using one-way ANOVA, showed that experimental groups (6, 7 and 8) were highly significant compared to the control groups 1 to 5 (p=0.0001).

CITED PUBLICATIONS

This description incorporates by reference each of the following publications:

Balicki & Beutler. Gene therapy of human disease. Medicine (Baltimore). 2002 January; 81(1):69-86.

Batra R K, Wang-Johanning F, Wagner E, Garver R I Jr, Curiel D T. Receptor-mediated gene delivery employing lectin-binding specificity. Gene Ther. 1994 July; 1(4):255-60.

Becker C M, Farnebo F A, Iordanescu I, Behonick D J, Shih M C, Dunning P, Christofferson R, Mulligan R C, Taylor G A, Kuo C J, Zetter B R. Gene therapy of prostate cancer with the soluble vascular endothelial growth factor receptor Flk1. Cancer Biol Ther. 2002 September-October; 1(5):548-53.

Bondoc, L L and Fitzpatrick S. Size distribution analysis of recombinant adenovirus using disc centrifugation. J Indust Micro Biotechnol. 20: 317-322 (1998).

Britton et al., "Characterization of a prokaryotic SMC protein involved in chromosome partitioning," Genes Dev. 12: 1254 (1998).

Carter, P. Improving the efficacy of antibody-based cancer therapies. Nat Rev Cancer. 2001 November; 1(2):118-29.

Ciliberto et al., "Cell-specific expression of a transfected human alpha 1-antitrypsin gene," Cell. 41: 531 (1985).

Conner S D, Schmid S L. Regulated portals of entry into the cell. Nature. 2003 Mar. 6; 422(6927):37-44.

Curiel et al., "Long-term inhibition of clinical and laboratory human immunodeficiency virus strains in human T-cell lines containing an HIV-regulated diphtheria toxin A chain gene," Hum. Gene Ther. 4: 741 (1993).

de Boer et al., "Roles of MinC and MinD in the site-specific septation block mediated by the MinCDE system of Escherichia coli," J. Bacteriol. 174: 63 (1992).

de Haard, H. J. et al. A large non-immunized human Fab fragment phage library that permits rapid isolation and kinetic analysis of high affinity antibodies. J. Biol. Chem. 274, 18218-18230 (1999).

Dinges et al., "HIV-regulated diphtheria toxin A chain gene confers long-term protection against HIV type 1 infection in the human promonocytic cell line U937," Hum. Gene Ther. 6: 1437 (1995).

Dubel S, Breitling F, Kontermann R, Schmidt T, Skerra A, Little M. Bifunctional and multimeric complexes of streptavidin fused to single chain antibodies (scFv). J. Immunol. Methods (1995) 178, 201-209.

Fernandez T, Bayley H. 1998. Ferrying proteins to the other side. Nat Biotechnol 16:418-430.

Frain et al., "Binding of a liver-specific factor to the human albumin gene promoter and enhancer," Mol. Cell Biol. 10: 991 (1990).

Glennie M J, McBride H M, Worth A T, Stevenson G T. Preparation and performance of bispecific Flab' gamma)2 antibody containing thioether-linked Fab' gamma fragments. J Immunol. 1987 Oct. 1; 139(7):2367-75.

Gosselin M A, Lee R J. Folate receptor-targeted liposomes as vectors for therapeutic agents. Biotechnol Annu Rev. 2002; 8:103-31.

Griffiths, A. D. et al. Isolation of high affinity human antibodies directly from large synthetic repertoires. EMBO J. 13, 3245-3260 (1994).

Grillot-Courvalin C, Goussard S, Courvalin P. Wild-type intracellular bacteria deliver DNA into mammalian cells. Cell Microbiol. 2002 March; 4(3):177-86.

Hanahan, Heritable formation of pancreatic beta-cell tumours in transgenic mice expressing recombinant insulin/simian virus 40 oncogenes. 1985 May 9-15; 315 (6015): 115-122.

Harrison et al., "Inhibition of human immunodeficiency virus-1 production resulting from transduction with a retrovirus containing an HIV-regulated diphtheria toxin A chain gene," Hum. Gene Ther. 3: 461 (1992a).

Harrison et al., "Inhibition of HIV production in cells containing an integrated, HIV-regulated diphtheria toxin A chain gene," AIDS Res. Hum. Retroviruses 8: 39 (1992b).

Harry, "Bacterial cell division: Regulating Z-ring formation," Mol. Microbiol. 40: 795 (2001).

Hart, "Tissue specific promoters in targeting systematically delivered gene therapy," Semin. Oncol. 23: 154 (1996).

Heim et al., "Wavelength mutations and posttranslational autoxidation of green fluorescent protein," Proc. Nat'l. Acad. Sci. USA 91: 12501 (1994).

Hiraga et al., "Chromosome partitioning in Escherichia coli: novel mutants producing anucleate cells," J. Bacteriol. 171: 1496 (1989).

Hoshida T, Sunamura M, Duda D G, Egawa S, Miyazaki S, Shineha R, Hamada H, Ohtani H, Satomi S, Matsuno S. Gene therapy for pancreatic cancer using an adenovirus vector encoding soluble flt-1 vascular endothelial growth factor receptor. Pancreas. 2002 August; 25(2):111-21.

Hu, S, L Shively, A Raubitschek, M Sherman, L E Williams, J Y Wong, J E Shively, and A M Wu. Minibody: A novel engineered anti-carcinoembryonic antigen antibody fragment (single-chain Fv-CH3) which exhibits rapid, high-level targeting of xenografts Cancer Res. 1996 56: 3055-3061.

Hu & Lutkenhaus, "Topological regulation of cell division in Escherichia coli involves rapid pole to pole oscillation of the division inhibitor MinC under the control of MinD and MinE," Mol. Microbiol. 34: 82 (1999).

Hudson, P. J. & Souriau, C. Recombinant antibodies for cancer diagnosis and therapy. Expert Opin. Biol. Ther. 1, 845-855 (2001).

Hudson P J, Souriau C. Engineered antibodies. Nat Med. 2003 January; 9 (1):129-34.

Hung M C, Hortobagyi G N, Ueno N T. Development of clinical trial of E1A gene therapy targeting HER-2/neu-overexpressing breast and ovarian cancer. Adv Exp Med Biol. 2000; 465:171-80.

Ireton et al., "spo0J is required for normal chromosome segregation as well as the initiation of sporulation in *Bacillus subtilis*," *J. Bacteriol*. 176: 5320 (1994).

Jones, P. T., Dear, P. H., Foote, J., Neuberger, M. S. & Winter, G. Replacing the complementarity-determining regions in a human antibody with those from a mouse. Nature 321, 522-525 (1986).

Katabi et al., "Hexokinase Type II: A Novel Tumor Specific Promoter for Gene-Targeted Therapy Differentially Expressed and Regulated in Human Cancer Cells," *Human Gene Therapy* 10: 155 (1999).

Kaetzel C S, Blanch V J, Hempen P M, Phillips K M, Piskurich J F, Youngman K R (1997): The polymeric immunoglobulin receptor: structure and synthesis. *Biochem Soc Trans* 25:475-480.

Karpovsky B, Titus J A, Stephany D A, Segal D M. Production of target-specific effector cells using hetero-cross-linked aggregates containing anti-target cell and anti-Fc gamma receptor antibodies. J Exp Med. 1984 Dec. 1; 160(6):1686-701.

Kelsey et al., "Species- and tissue-specific expression of human alpha 1-antitrypsin in transgenic mice," *Genes and Devel*. 1: 161 (1987).

Kerem et al., "Identification of the cystic fibrosis gene: genetic analysis," *Science* 245: 1073 (1989).

Khare, P. D. et al. Tumor growth suppression by a retroviral vector displaying scFv antibody to CEA and carrying the iNOS gene. Anticancer Res. 22, 2443-2446 (2002).

Kleeff J, Fukahi K, Lopez M E, Friess H, Buehler M W, Sosnowski B A, Korc M. Targeting of suicide gene delivery in pancreatic cancer cells via FGF receptors. Cancer Gene Ther. 2002 June; 9(6):522-32.

Knappik, A. et al. Fully synthetic human combinatorial antibody libraries (HuCAL) based on modular consensus frameworks and CDRs randomized with trinucleotides. J. Mol. Biol. 296, 57-86 (2000).

Kostelny S A, Cole M S, Tso J Y. Formation of a bispecific antibody by the use of leucine zippers. J Immunol. 1992 Mar. 1; 148(5):1547-53.

Kurane et al., "Targeted Gene Transfer for Adenocarcinoma Using a Combination of Tumor specific Antibody and Tissue-specific Promoter," *Jpn. J. Cancer Res*. 89: 1212 (1998).

Levin et al., "Identification of *Bacillus subtilis* genes for septum placement and shape determination," *J. Bacteriol*. 174: 6717 (1992).

Leder et al., "Consequences of widespread deregulation of the c-myc gene in transgenic mice: multiple neoplasms and normal development," *Cell* 45: 485 (1986).

MacDonald et al., "Expression of the pancreatic elastase I gene in transgenic mice," *Hepatology* 7: 425 (1987).

Marshall. Carcinoembryonic antigen-based vaccines. Semin. Oncol. 2003 June; 30 (3 Suppl. 8): 30-36.

Mason et al., "The hypogonadal mouse: reproductive functions restored by gene therapy," *Science* 234: 1372 (1986).

Morton & Potter, "Rhabdomyosarcoma-specific expression of the herpes simplex virus thymidine kinase gene confers sensitivity to ganciclovir," *J. Pharmacology & Exper. Therapeutics* 286: 1066 (1998).

Okada et al., "Possible function of the cytoplasmic axial filaments in chromosomal segregation and cellular division of *Escherichia coli*," *Sci. Prog*. 77: 253 (1993-94).

Okada et al., "Cytoplasmic axial filaments in *Escherichia coli* cells: possible function in the mechanism of chromosome segregation and cell division," *J. Bacteriol*. 176: 917 (1994).

Osbourn, J., Jermutus, L., Duncan, A. Current methods for the generation of human antibodies for the treatment of autoimmune diseases. Drug Delivery Tech 8: 845-851 (2003).

Pack P, Pluckthun A. Miniantibodies: use of amphipathic helices to produce functional, flexibly linked dimeric Fv fragments with high avidity in *Escherichia coli*. Biochemistry. 1992 Feb. 18; 31(6):1579-84.

PCT IB02/04632

Phelan A, Elliott G, O'Hare P. 1998. Intercellular delivery of functional p53 by the herpesvirus protein VP22. Nat Biotechnol 16:440-443.

Pinkert et al., "An albumin enhancer located 10 kb upstream functions along with its promoter to direct efficient, liver-specific expression in transgenic mice," *Genes and Devel*. 1: 268 (1987).

Prasher et al., "Using GFP to see the light," *Trends in Genetics* 11: 320 (1995).

Ragheb et al., "Inhibition of human immunodeficiency virus type 1 by Tat/Rev-regulated expression of cytosine deaminase, interferon alpha2, or diphtheria toxin compared with inhibition by transdominant Rev," *Hum. Gene Ther*. 10: 103 (1999).

Raskin & de Boer, "MinDE-dependent pole-to-pole oscillation of division inhibitor MinC in *Escherichia coli*," *J. Bacteriol*. 181: 6419 (1999).

Readhead et al., "Myelin deficient mice: expression of myelin basic protein and generation of mice with varying levels of myelin," *Cell* 48: 703 (1987).

Reeve, "Use of minicells for bacteriophage-directed polypeptide synthesis," *Methods Enzymol*. 68: 493 (1979).

Reeve & Cornett. Bacteriophage SPO1-induced macromolecular synthesis in minicells of *Bacillus subtilis*. J. Virol. 1975 June; 15(6):1308-16.

Ridgway J B, Presta L G, Carter P. 'Knobs-into-holes' engineering of antibody CH3 domains for heavy chain heterodimerization. Protein Eng. 1996 July; 9(7):617-21.

Riechmann, L., Clark, M., Waldmann, H. & Winter, G. Reshaping human antibodies for therapy. Nature 332, 323-327 (1988).

Riordan et al., "Identification of the cystic fibrosis gene: cloning and characterization of complementary DNA," *Science* 245: 1066 (1989).

Rojas M, Donahue J P, Tan Z, Lin Y Z. 1998. Genetic engineering of proteins with cell membrane permeability. Nat Biotechnol 16(4): 370-375.

Romano et al., Gene transfer technology in therapy: current applications and future goals. Stem Cells. 1999; 17(4): 191-202.

Romano et al., Recent advances, prospects and problems in designing new strategies for oligonucleotide and gene delivery in therapy. In Vivo. 1998 January-February; 12(1):59-67.

Rommens et al., "Identification of the cystic fibrosis gene: Chromosome walking and jumping," *Science* 245: 1059 (1989).

Salomon D S, Brandt R, Ciardiello F, Normanno N. Epidermal growth factor-related peptides and their receptors in human malignancies. Crit Rev Oncol Hematol 1995, 19, 183-232.

Shangara et al., "Suicide genes: past, present and future perspectives," *Immunology Today* 21: 48 (2000).

Sheets, M. D. et al. Efficient construction of a large nonimmune phage antibody library: the production of high-affinity human single-chain antibodies to protein antigens. Proc. Natl Acad. Sci. USA 95, 6157-6162 (1998).

Singh, Transferrin as a targeting ligand for liposomes and anticancer drugs. Curr Pharm Des. 1999 June; 5(6):443-51.

Singhal and Kaiser, Cancer chemotherapy using suicide genes. Surg Oncol Clin N Am. 1998 July; 7(3):505-36.

Spencer, "Developments in suicide genes for preclinical and clinical applications," *Molecular Therapeutics* 2: 433 (2000).

Stewart & D'Ari, "Genetic and morphological characterization of an *Escherichia coli* chromosome segregation mutant," *J. Bacteriol.* 174: 4513 (1992).

Stockert. The asialoglycoprotein receptor: relationships between structure, function, and expression. Physiol Rev. 1995 July; 75(3):591-609.

Swift et al., "Tissue-specific expression of the rat pancreatic elastase I gene in transgenic mice," *Cell* 38: 639 (1984).

Thomas, C. E., Edwards, P., Wickham, T. J., Castro, M. G. & Lowenstein, P. R. Adenovirus binding to the coxsackievirus and adenovirus receptor or integrins is not required to elicit brain inflammation but is necessary to transduce specific neural cell types. J. Virol. 76, 3452-3460 (2002).

Thomas C E, Ehrhardt A, Kay M A. Progress and problems with the use of viral vectors for gene therapy. Nat Rev Genet. 2003 May; 4(5):346-58.

Thurnher M, Wagner E, Clausen H, Mechtler K, Rusconi S, Dinter A, Birnstiel M L, Berger E G, Cotten M. Carbohydrate receptor-mediated gene transfer to human T leukaemic cells. Glycobiology. 1994 August; 4(4):429-35.

Todorovska, A. et al. Design and application of diabodies, triabodies and tetrabodies for cancer targeting. J. Immunol. Methods 248, 47-66 (2001).

Tomlinson, I. & Holliger, P. Methods for generating multivalent and bispecific antibody fragments. Methods Enzymol. 326, 461-479 (2000).

Vaughan, T. J. et al. Human antibodies with subnanomolar affinities isolated from a large non-immunized phage display library. Nature Biotechnol. 14, 309-314 (1996).

Vaughan, T. J., Osbourn, J. K. & Tempest, P. R. Human antibodies by design. Nature Biotechnol. 16, 535-539 (1998).

Verhoeyen, M., Milstein, C. & Winter, G. Reshaping human antibodies: grafting an antilysozyme activity. Science 239, 1534-1536 (1988).

Wachi et al., "New mre genes mreC and mreD, responsible for formation of the rod shape of *Escherichia coli* cells," *J. Bacteriol.* 171: 6511 (1989).

Wadhwa. Cancer gene therapy: scientific basis. Annu. Rev. Med. 2002; 53:437-52.

Wickham. Ligand-directed targeting of genes to the site of disease. Nat Med. 2003 January; 9(1):135-9.

Yazawa et al., "Current progress in suicide gene therapy for cancer," *World J. Surg.* 26: 783 (2002).

Ziady A G, Perales J C, Ferkol T, Gerken T, Beegen H, Perlmutter D H, Davis P B. Gene transfer into hepatoma cell lines via the serpin enzyme complex receptor. Am J Physiol. 1997 August; 273(2 Pt 1):G545-52.

What is claimed is:

1. A composition comprising:
   (i) an effective dose of purified, intact bacterially derived minicells comprising a therapeutic nucleic acid molecule, wherein the dose is free of contamination removable through 200 nm filtration, and wherein the minicells are approximately 400 nm in diameter;
   (ii) a bispecific antibody or antibody fragment having specificity for a cancer cell surface receptor and the minicell, wherein the bispecific antibody or antibody fragment is bound to the minicell; and
   (iii) a pharmaceutical acceptable carrier;
   wherein the bispecific antibody or antibody fragment comprises a first multivalent arm that carries specificity for a bacterially derived minicell surface structure and a second multivalent arm that carries specificity for a cancer cell surface receptor, wherein the cancer cell surface receptor is capable of activating receptor-mediated endocytosis of the minicell.

2. The composition of claim 1, wherein said first arm and said second arm are monospecific.

3. The composition of claim 1, wherein said minicell surface structure is an O-polysaccharide component of a lipopolysaccharide on said minicell surface.

4. The composition of claim 1, wherein said minicell surface structure is selected from the group consisting of outer membrane proteins, pilli, fimbrae, flagella, and cell-surface exposed carbohydrates.

5. The composition of claim 1, wherein said bispecific antibody or antibody fragment comprises a humanized antibody.

6. The composition of claim 1, wherein said minicell comprises an intact cell wall.

7. The composition of claim 1, wherein said therapeutic nucleic acid sequence comprises a suicide gene.

8. The composition of claim 1, wherein said therapeutic nucleic acid encodes a normal counterpart of a protein that functions abnormally or is present in abnormal levels in said cell.

9. The composition of claim 1, wherein said therapeutic nucleic acid is contained on a plasmid.

10. The composition of claim 9, wherein said plasmid comprises a regulatory element.

11. The composition of claim 9, wherein said plasmid comprises a reporter element.

12. The composition of claim 1, wherein the minicells are purified using a combination of gradient centrifugation, filamentation, and/or filtration.

13. The composition of claim 1, wherein the minicells are purified to remove endotoxin.

14. The composition of claim 1, wherein the minicells are purified using a combination of gradient centrifugation, filamentation, and/or filtration and to remove endotoxin.

* * * * *